US011937587B2

(12) United States Patent
Olson et al.

(10) Patent No.: US 11,937,587 B2
(45) Date of Patent: *Mar. 26, 2024

(54) NON-HUMAN ANIMALS EXPRESSING HUMANIZED CD3 COMPLEX

(71) Applicant: Regeneron Pharmaceuticals, Inc., Tarrytown, NY (US)

(72) Inventors: Kara L. Olson, White Plains, NY (US); Eric Smith, New York, NY (US); Ka-Man Venus Lai, Seattle, WA (US); Andrew J. Murphy, Croton-on-Hudson, NY (US); Gavin Thurston, Millerton, NY (US); Dayong Guo, Overland Park, KS (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 546 days.

This patent is subject to a terminal disclaimer.

(21) Appl. No.: 17/118,241

(22) Filed: Dec. 10, 2020

(65) Prior Publication Data

US 2021/0100229 A1 Apr. 8, 2021

Related U.S. Application Data

(63) Continuation of application No. 16/872,226, filed on May 11, 2020, now Pat. No. 10,932,455, which is a continuation of application No. 14/949,834, filed on Nov. 23, 2015, now abandoned.

(60) Provisional application No. 62/106,999, filed on Jan. 23, 2015, provisional application No. 62/083,653, filed on Nov. 24, 2014.

(51) Int. Cl.
*A01K 67/027* (2006.01)
*C07K 14/725* (2006.01)
*C12N 5/071* (2010.01)
*C12N 15/85* (2006.01)
*G01N 33/50* (2006.01)

(52) U.S. Cl.
CPC ...... *A01K 67/0278* (2013.01); *A01K 67/0276* (2013.01); *C07K 14/7051* (2013.01); *C12N 5/0602* (2013.01); *C12N 15/8509* (2013.01); *G01N 33/5088* (2013.01); *A01K 2207/12* (2013.01); *A01K 2207/15* (2013.01); *A01K 2217/072* (2013.01); *A01K 2217/075* (2013.01); *A01K 2217/15* (2013.01); *A01K 2227/105* (2013.01); *A01K 2267/01* (2013.01); *A01K 2267/03* (2013.01); *A01K 2267/0337* (2013.01); *Y02A 50/30* (2018.01)

(58) Field of Classification Search
CPC .................. A01K 67/0278; C07K 14/7051
USPC ....................................................... 536/23.1
See application file for complete search history.

(56) References Cited

U.S. PATENT DOCUMENTS

| | | |
|---|---|---|
| 7,888,121 B2 | 2/2011 | Urnov et al. |
| 8,106,255 B2 | 1/2012 | Carroll et al. |
| 10,822,420 B2 | 11/2020 | Jishage et al. |
| 2005/0066375 A1 | 3/2005 | Thiam et al. |
| 2012/0117671 A1 | 5/2012 | Yoneyama et al. |
| 2013/0111616 A1 | 5/2013 | MacDonald et al. |
| 2013/0111617 A1 | 5/2013 | MacDonald et al. |
| 2013/0117873 A1 | 5/2013 | Wang et al. |
| 2013/0130388 A1 | 5/2013 | Murphy et al. |
| 2014/0134662 A1 | 5/2014 | Flavell et al. |
| 2014/0245466 A1 | 8/2014 | MacDonald et al. |
| 2014/0245467 A1 | 8/2014 | MacDonald et al. |
| 2015/0089678 A1 | 3/2015 | Murphy et al. |
| 2015/0143558 A1 | 5/2015 | McWhirter et al. |
| 2015/0266966 A1 | 9/2015 | Smith et al. |
| 2015/0282463 A1 | 10/2015 | Murphy et al. |
| 2015/0320021 A1 | 11/2015 | Wang et al. |
| 2015/0327524 A1 | 11/2015 | Murphy et al. |
| 2015/0342163 A1 | 12/2015 | Voronina et al. |
| 2015/0366174 A1 | 12/2015 | Burova et al. |

FOREIGN PATENT DOCUMENTS

| | | |
|---|---|---|
| EP | 2155783 B1 | 7/2013 |
| WO | 2003/006639 A1 | 1/2003 |
| WO | 2008/119566 A2 | 10/2008 |
| WO | 2014/028776 A1 | 2/2014 |
| WO | 2014/047231 A1 | 3/2014 |
| WO | 2014/056783 A1 | 4/2014 |
| WO | 2014/130671 A1 | 8/2014 |
| WO | 2014/130671 A8 | 8/2014 |

OTHER PUBLICATIONS

Amann et al., "Therapeutic window of an EpCAM/CD3-Specific BiTE antibody in mice is determined by a subpopulation of EpCAM-expressing lymphoctes that is absent in humans," Cancer Immunol. Immunother., 58:95-109 (2009).

Amann et al., "Antitumor Activity of an EpCAM/CD3-bispecifi BiTE Antibody During Long Term Treatment of Mice in the Absence of T-cell Anergy and Sustained Cytokine Release," J. Immunother., 32(5):452-464 (2009).

(Continued)

*Primary Examiner* — Valarie E Bertoglio
(74) *Attorney, Agent, or Firm* — FisherBroyles, LLP; Rita S. Wu; Casey Donahoe

(57) ABSTRACT

Non-human animals, expressing humanized CD3 proteins are provided. Non-human animals, e.g., rodents, genetically modified to comprise in their genome humanized CD3 proteins are also provided. Additionally, provided are methods and compositions of making such non-human animals, as well as methods of using said non-human animals.

19 Claims, 15 Drawing Sheets

Specification includes a Sequence Listing.

(56) References Cited

OTHER PUBLICATIONS

Amann et al., "Therapeutic Window of MuS110, a Single-Chain Antibody Construct Bispecific for Murine EpCAM and Murine CD3," Cancer Res., 68(1):143-151 (2008).
Brevini et al., (2010) "No shortcuts to pig embryonic stem cells," Theriogenology 74:544-550.
Cao et al., (2009) "Isolation and Culture of Primary Bovine Embryonic Stem Cell Colonies by a Novel Method," Journal of Experimental Zoology, 311A:368-376.
Cohen et al., (2006) "Enhanced Antitumor Activity of Murine-Human Hybrid T-Cell Receptor (TCR) in Human Lymphocytes Is Associated with Improved Pairing and TCR/CD3 Stability," Cancer Res., Sep. 1, 2006, 66:8878-8886.
Cole et al., "HuM291, A Humanized Anti-Cd3 Antibody, is Immunosuppressive to T Cells while Exhibiting Reduced Miotgenicity in Vitro," Transplantation, 68(4):563-571 (1999).
Dave, "Hierarchial role of CD3 chains in the thomocyte development," Immunological Reviews, 232:22-33 (2009).
De La Hera et al., "Structure of the T Cell Antigen Receptor (TCR): Two CD3ε Subunits in a Functional TCR/CD3 Complex," J. Exp. Med., 173:7-17 (1991).
Dennis (2002) "Welfare issues of genetically modified animals," ILAR Journal, 43(2):100-109.
Fernandez-Malve et al., "Overlapping functions of human CD3δ and mouse CD3γ in a αβ T-cell development revealed in a humanized CD3γ deficient mouse," Blood, 108(10):3420-3427 (2006).
GenBank Accession No. AY890876 (Mar. 2005) https://www.ncbi.nlm.nih.gov/nuccore/AY890876 accessed on Sep. 1, 2017.
GenBank Accession No. AK311971 (May 2008) https://www.ncbi.nlm.nih.go/nuccore/AK311971 accessed on Sep. 1, 2017.
GenBank Accession No. AK313966 (May 2008) https://www.ncbi.nlm.nih.go/nuccore/AK313966 accessed on Sep. 1, 2017.
GenBank Accession No. NP_000064 https://www.ncbi.nlm.nih.gov/protein/NP_000064.
GenBank Accession No. NP_031674 https://www.ncbi.nlm.nih.gov/protein/NP_031674.
GenBank Accession No. NP_033980 https://www.ncbi.nlm.nih.gov/protein/NP_033980.
GenBank Accession No. NP_038515 https://www.ncbi.nlm.nih.gov/protein/NP_038515.
GenBank Accession No. NP_000723 https://www.ncbi.nlm.nih.gov/protein/NP_000723.
GenBank Accession No. NP_000724 https://www.ncbi.nlm.nih.gov/protein/NP_000724.
Gobel and Dangy, "Evidence for a Stepwise Evolution of the CD3 Family," J. Immunol., 164:879-883 (2000).
Gobel et al., "Biochemical analysis of the Xenopus laevis TCR/CD3 complex supports the "stepwise evolution" model," Eur. J. Immunol., 30:2775-2781 (2000).
Harari et al., "Bridging the Species Divide: Transgenic Mice Humanized for Type-I Interferon Response," PLOS One, Jan. 2014, 9(1):e84259, 12 pages.
Hennecke and Wiley, "T Cell Receptor-MHC Interactions up Close," (Jan. 12, 2001) Cell, 104:1-4.
Houdebine (2009) Methods to Generate Transgenic Animals, Genetic Engineering in Livestock, New Applications and Interdisciplinary Perspectives, Engelhard M, et al., 2009, XVI, 1 46 p. 8 illus., pp. 31-47, see p. 36.
Kim et al., "Distinctive CD3 Heterodimeric Ectodomain Topologies Maximize Antigen-Triggered Activation of αβ T Cell Receptors," J. Immunol., 185(5):2951-2959 (2010).
Kuhn et al., "Human CD3 Transgenic Mice: Preclinical Testing of Antibodies Promoting Immune Tolerance," Sci. Transl. Med., 3(68):1-9 (2011).
Kuhns and Davis "TCR signaling emerges from the sum of many parts," Front. Immunol., https://doi.org/10.3389/fimmu.2012.00159 (13 pages).
Kuhns et al., "Deconstructing the Form and Function of the TCR/CD3 Complex," Immunity, 24:133-139 (2006).

Letourneur et al. "The mouse CD3-γ, -δ, and -ε genes reside within 50 kilobases on chromosome 9, whereas CD3-ζ maps to chromosome 1, band H," Immunogenetics, (1989) 29:265-268.
Marten (2003) "Transgenic mouse methods and protocols," Methods in Molecular Biology, 209:51-58 and English translation.
Ohigashi et al. "Identification of the Transgenic Integration Site in Immunodeficient tgε26 Human CD3ε Transgenic Mice," PLoS One 5(12):e14391 (Dec. 2010) (7 pages).
Pan et al., "Different role for mouse and human CD3δ/ε heterodimer in pre T cell receptor (preTCR) function: Human CD3δ/ε heterodimer restores the defective preTCR function in CD3γ- and CD3γδ-deficient mice," Molecular Immunology 43:1741-1750 (2006).
Paris and Stout (2010) "Equine embryos and embryonic stem cells: Defining reliable markers of pluripotency," Theriogenology 74:516-624.
Rao et al., "OKT3E, An Anti-CD3 Antibody that Does Not Elicit Side Effects or Antiidiotype Responses in Chimpanzees," Transplantation, 52(4):691-697 (1991).
Risueño et al. "A conformational change senses the strength of T cell receptor-ligand interaction during thymic selection," PNAS, (Jun. 20, 2006) 103(25):9625-9630.
Rybchin V.N., (2002) "Basics of Genetic Engineering," Saint-Petersburg, Publishing House of Saint-Petersburg State Technology Institute, p. 411-413.
Shiheido et al., "Modulation of the Human T Cell Response by a Novel Non-Mitogenic Anit-CD3 Antibody," PLoS One, 9(4):1-9 (2014).
Sun et al., "Anti-CD20/CD3 T cell-dependent bispecific antibody for the treatment of B cell malignancies," Immunotherapy, 7(287):1-10 (2015).
Tunnacliffe et al., "The majority of human CD3 epitopes are conferred by the epsilon chain," International Immunology, 1(5):546-550 (1989).
Ueda et al., "Entire CD3ε, δ, and γ humanized mouse to evaluate human CD3-mediated therapeutics," Nature, Scientific Reports, 7:45839 (Apr. 2017) DOI: 10.1038/srep45839 with Corrigendum 8:46960 (16 pages).
Wang et al., "A block in both early T lymphocyte and natural killer cell development in transgenic mice with high-copy numbers of the human CD3E gene," Proc. Natl. Acad. Sci. USA, 91:9402-9406 (1994).
Wang et al., "CD3-ε Overexpressed in Prothymocytes Acts as an Oncogene," Molecular Medicine, 3(1)72-81 (Jan. 1997).
Wang et al., "Expression of a CD3ε transgene in CD3ε$^{null}$ mice does not restore CD3γ and δ expression but efficiently rescues T cell development from a subpopulation of prothymocytes," International Immunology, 10(12)1777-1788 (1998).
Watson and Crick (2002) Molekulyarnaya biotekhnologiya. Printsipy i primeneniye, Moscow Mir., 45-47 and English translation.
Weidle et al., Tumor-Antigen-Binding Bispecific Antibodies for Cancer Treatment, Semin Oncol., 41(5):653-660 (2014).
Xu et al., "A Membrane-proximal Tetracysteine Motif Contributes to Assembly of CD3δε and CD3γε Dimers with the T Cell Receptor," Journal of Biological Chemistry, 281(48):36977-36984 (Dec. 1, 2006).
Zhou et al., (2009) "Developing tTA transgenic rats for inducible and reversible gene expression," International Journal of Biological Sciences, 5:171-181.
International Search Report and Written Opinion of the International Searching Authority with respect to PCT/US2015/062229, dated Mar. 14, 2016.
English Translation of the Office Action dated Jun. 26, 2019 with respect to Russia Patent Application No. 2017122038.
Christian, M., et al., "Targeting DNA Double-Strand Breaks with TAL Effector Nucleases," Genetics, 186:757-761 (2010).
Ezashi, T., et al., "Pluripotent Stem Cells from Domesticated Mammals," Annu. Rev. Anim. Biosci., 4:223-253 (2016).
Geurts, A. M., et al., Author Manuscript "Knockout Rats Produced Using Designed Zinc Finger Nucleases," Science, 325(5939):433 (2009).
Hauschild, J., et al., "Efficient generation of a biallelic knockout in pigs using zinc-finger nucleases," PNAS, 108(29):12013-12017 (2011).

(56) References Cited

OTHER PUBLICATIONS

Hong, J., et al., "Derivation and Characterization of Embryonic Stem Cells Lines Derived from Transgenic Fischer 344 and Dark Agouti Rats," Stem Cells Dev., 21(9):1571-1586 (2012).
Patil, V. M., et al., "Transgenic animals and drug development: A review," Indian Journal of Public Health Research & Development, 2(1):106-109 (2011).
Ramirez, C. L., et al., Author Manuscript "Unexpected failure rates for modular assembly of engineered zinc fingers," Nat. Methods, 5(5):374-375 (2008).
Selsby, J. T., et al., "Porcine Models of Muscular Dystrophy," Ilar J., 56(1):116-126 (2015).
Tong et al., "Production of p53 gene knockout rats by homologous recombination in embryonic stem cells," Nature, 467:211-215 (Sep. 9, 2010).
Willinger, T., et al., "Improving human hemato-lymphoid-system mice by cytokine knock-in gene replacement," Trends Immunol., 32(7):321-327 (2011).

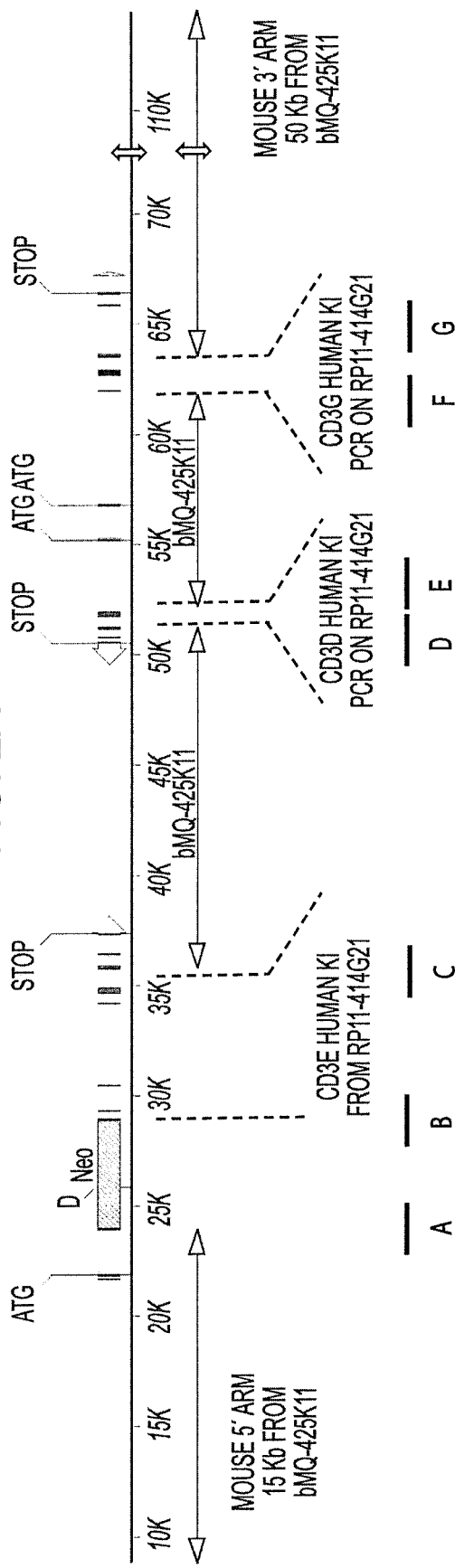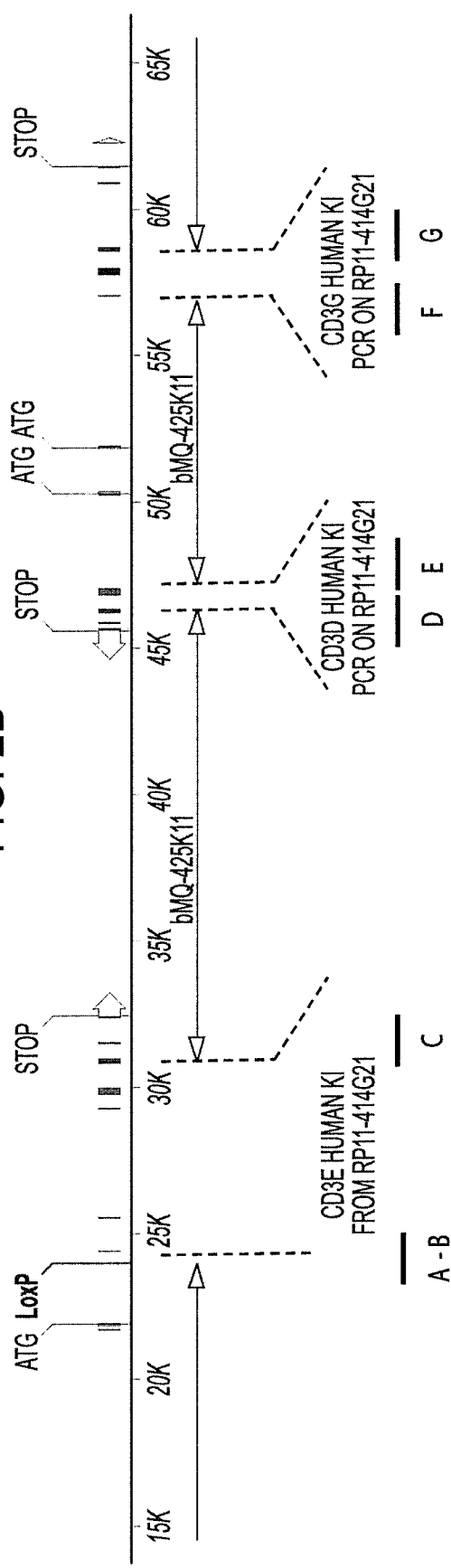

FIG. 3

CD3e humanized protein
(SEQ ID NO: 24)

MRWNTFWGILCLSLLAVGVWGQDGNEEMGGITQTPYKVSISGTTVILTCPQ
YPGSEILWQHNDKNIGGDEDDKNIGSDEDHLSKEFSELEQSGYYVCYPRGSK
PEDANFYLYLRARVCENCMEMDVMSVAIIIVDICITLGLLMVIYYWSKNRKAK
AKPVTRGTGAGSRPRGQNKERPPPVPNPDYEPIRKGQRDLYSGLNQRAV*

CD3d humanized protein
(SEQ ID NO:25)

MEHSGILASLILIAVLPQVSPFKIPIEELEDRVFVNCNTSITWVEGTVGTLLSDITRL
DLGKRILDPRGIYRCNGTDIYKDKESTVQVHYRMCQSCVELDPATVAGVIFIDLIA
TLLLALGVYCFAGHETGRPSGAAEVQALLKNEQLYQPLRDREDTQYSRLGGNWP
RNKKS*

CD3g humanized protein
(SEQ ID NO:26)

MEQRKGLAGLFLVISLLQGTLAQSIKGNHLVKVYDYQEDGSVLLTCDAEAKNIT
WFKDGKMIGFLTEDKKKWNLGSNAKDPRGMYQCKGSQNKSKPLQVYYRMC
QNCIELNAATISGFIFAEVISIFFLALGVYLIAGQDGVRQSRASDKQTLLQNEQLY
QPLKDREYDQYSHLQGNQLRKK*

Underscored residues coded by introduced human exons

FIG. 4 mCd3e/hCD3E protein alignment

```
mCD3ep    1 MRWNTFWGLLCLSLLAVGTCQDDAEN------IEYKVSISGTSVELTCPLDSDENLKWEKNGQELP-QKHDK------HLVLQDFSEVEDSGYYVCYT  85
hCD3ep    1 MQSGTHWRVLGLCLLSVGVWGQDGNEEMGGIQTPYKVSISGTTVILTCPQYPGSEILWQHNDKNIGGDEDHLSLKEFSELEQSGYYVCYP        100
            *.*.*..*.*.******..*              ********.*.*.      **    * ****.*  *********** mCD3ep   86 PAS---NKNTYLYLKARVCEYCVEVDLTAVAIIIVDICITLGLLMVIYWSKNRKAKAKPVTRGTGAGSRPRGQNKERPPVPNPDYEPIRKGQRDLYS  182
hCD3ep  101 RGSKPEDANFYLYLRARVCENCMEMDVMSVATIVIVDICITLGGLLLLVYWSKNRKAKAKPVTRGAGAGGRQRGQNKERPPVPNPDYEPIRKGQRDLYS  200
            * *    *.*.*****.*.* *. * ..**** ...* *****************...************* mCD3ep  183 GLNQRAV 189
hCD3ep  201 GLNQRRI 207
            *****.
``` mCd3d/hCD3D protein alignment

```
mCd3d        1 MEHSGIIASLIIAVLPQGSPFKIQVTEYEDKVFVTCNTSVMHLDGTVEGWFAKNKTLNLGKGVLDPRGIYLCNGTEQLAKVVSSVQVHYRMCQNCVELD  100
hCD3D        1 MEHSTFLSGLVIATLLSQVSPFKIPIEELEDRVFVNCNTSITWVEGTVGTLLSDITRLDLGKRILDPRGIYRCNGTDIYDKESTVQVHYRMCQSCVELD  100
               ****    *.*.** *.*.******.  .* **.** ****.   **.  .***  .* **** ********* ****..  *.**********.****

mCd3d      101 SGTMAGVIFIDLIATLLLALGVYCFAGHETGRPSGAAEVQALLKNEQLYQPLREDTQYSRLGGNWPRNKKS 173
hCD3D isoA 101 PATVAGIIVTDVIATLLALGVFCFAGHETGRLSGAADTQALLRNDQVYQPLRDRDDAQYSHLGGNWARNK-- 171
               .*..** .   ****** ****.********* ****  ****.*..****..*.. **.*****.**
``` mCd3g/hCD3G protein alignment

```
mCd3g    1 MEQRKGLAGLFLIVISLLQGTVAQTNKAKNLIVQDGSRGRDGSVLLTCGLTDKTIKWLKDGSIISPLNATKNTWNLGNNAKDPRGTYQCQGAKETSNPLQVY  100
hCD3G    1 MEQGKGLAVLILAIIILLQGTLAQSIKGNHLVKVYDYQEDGSVLLTCDAEAKNITWFKDGKMIGFLTEDKKWNLGSNAKDPRGMYQCKGSQNKSKPLQVY  100
           * **.* *.*.* ***... *.**.* * . .***** *   . *.*..*.* ..**.*.*..*.***** mCd3g  101 YRMCENCIELNIGTISGFIPAEVISIFFLALGVLIAGQDGVRQSRASDKQTLLQNEQLYQPLKDREYDQYSHLQGNQLRKK 182
hCD3G  101 YRMCQNCIELNAATISGFLFAEIVSIFVLAVGVVFIAGQDGVRQSRASDKQTLLPNDQLYQPLKDREDDQYSHLQGNQLRRN 182
           ****.******  ***** ***.*** **.**. *****************.*.**********  ***********..
```

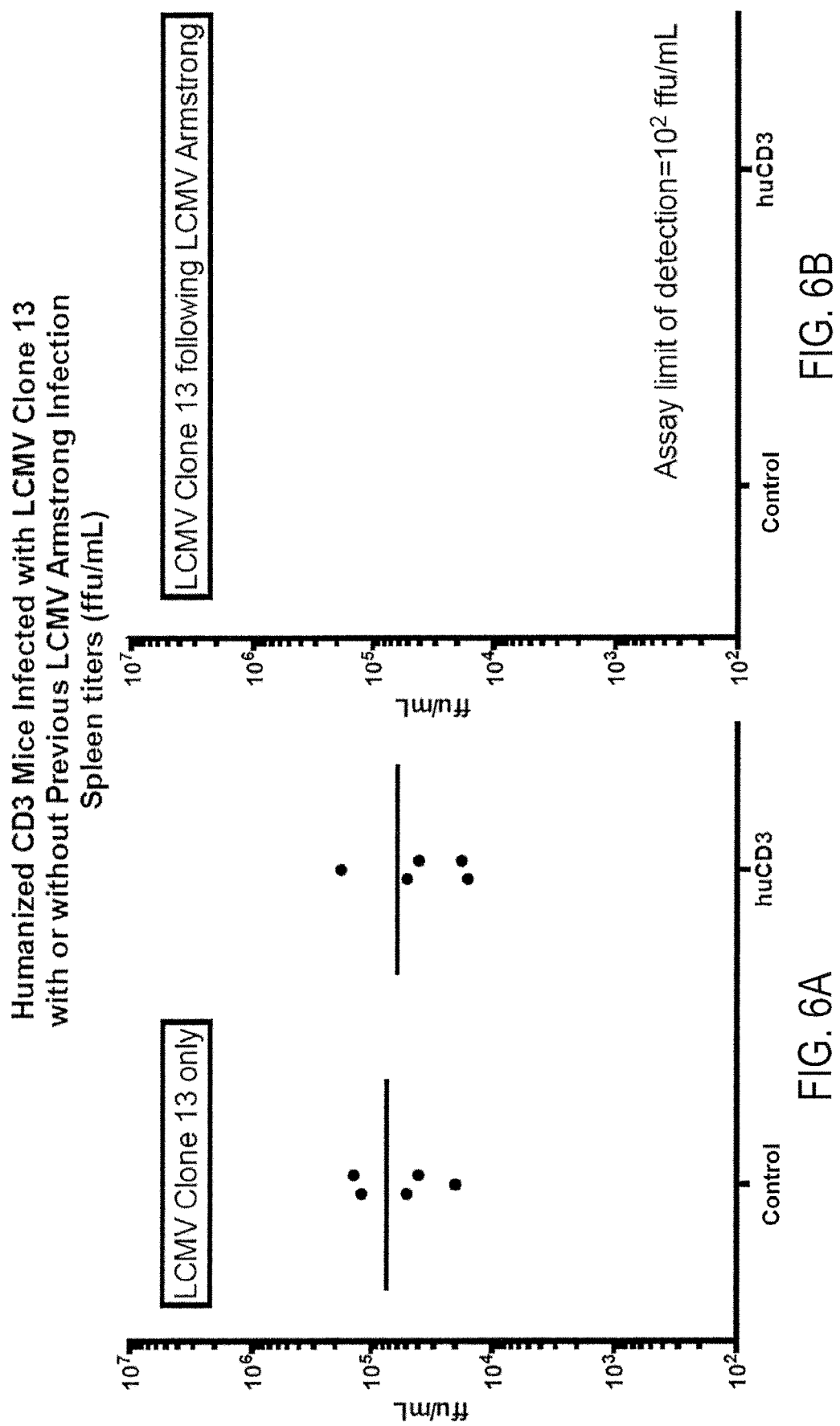

- ah/mf = anti-human CD3 antibodies that cross-react to cynomolgus monkey CD3
- ah = anti-human CD3 antibodies that do not cross-react to cynomolgus monkey CD3

FIG. 10

| Genotype | ECD | T cell development | Responds to anti-mCD3 | Binds anti-hCD3 | Responds to anti-hCD3 |
|---|---|---|---|---|---|
| WT | Mouse | Normal | Yes | No | No |
| hCD3gde-homozygous | Human | Normal | No | Yes, all antibodies tested, including cynomolgus monkey cross-reacting antibodies | Yes, all antibodies tested, including cynomolgus monkey cross-reacting antibodies |

** - compared to vehicle; * - compared to Control Ab 2 control
Data represents the composite data from n=5 mice per group. Data are expressed as mean (SEM) and were analysed using analysis of variance (ANOVA) and post hoc tests to probe significant effects (Tukey's for two-way ANOVA).

NON-HUMAN ANIMALS EXPRESSING HUMANIZED CD3 COMPLEX

CROSS-REFERENCE TO RELATED APPLICATIONS

The present application is a continuation of U.S. patent application Ser. No. 16/872,226, filed May 11, 2020, which is a continuation of U.S. patent application Ser. No. 14/949,834, filed Nov. 23, 2015, which is a nonprovisional of 62/083,653 filed Nov. 24, 2014 and 62/106,999 filed Jan. 23, 2015, each incorporated by reference in its entirety for all purposes.

REFERENCE TO A SEQUENCE LISTING

The application includes sequences in a txt file named 470382_SEQLST.txt, created Nov. 23, 2015 and of 23,965 bytes, which is incorporated by references.

FIELD OF INVENTION

A genetically modified non-human animal (e.g., a rodent, e.g., a mouse or a rat) is provided that comprises in its genome a nucleic acid sequence encoding a humanized CD3 protein, e.g., a humanized CD3ε, a humanized CD3δ, and/or humanized CD3γ. Thus, genetically modified non-human animals that express humanized CD3 complex are provided. Also provided herein is a model for preclinical testing of CD3-based therapeutics, e.g., CD3-based antibodies, e.g., CD3-based bispecific antibodies.

BACKGROUND OF THE INVENTION

In addition to the T cell receptor subunits, e.g., highly variable TCRα and TCRβ, the T cell receptor complex on the surface of a T cell comprises invariant CD3ε, CD3δ, and CD3γ chains, which form heterodimers consisting of CD3εδ and CD3εγ. Also associated with the TCR/CD3 complex is the ζ chain, which is present as a disulfide-linked homodimer.

CD3 chains play a crucial role in T cell receptor assembly, transport to the cell surface, endocytosis of surface receptors, T cell development, and T cell signaling. For example, it has been demonstrated through studies of deficiencies of various CD3 subunits, that CD3 chains are important for double negative (CD4−CD8− or DN) to double positive (CD4+CD8+ or DP) to single positive (CD4+ or CD8+ or SP) T cell transition. In addition, each of CD3ε, CD3δ, and CD3γ chains contains one immunoreceptor tyrosine-based activation motif (ITAM) while the chain dimer contains 6 total ITAMs. These motifs serve as signaling modules, and are phosphorylated by associated kinases upon TCR engagement.

Antibodies against CD3 have been shown to cluster CD3 on 1' cells, thereby causing T cell activation in a manner similar to the engagement of the TCR by peptide-loaded MHC molecules. Thus, anti-CD3 antibodies have been proposed as therapeutic candidates aimed at activation of T cells. In addition, bispecific antibodies that are capable of binding CD3 and a target antigen have been proposed for therapeutic uses involving targeting T cell immune responses to tissues and cells expressing the target antigen.

A convenient animal model for preclinical testing of mono- and bispecific CD3-based therapeutic antibodies is particularly desired.

SUMMARY OF THE INVENTION

Provided herein is a genetically modified non-human animal comprising an endogenous non-human CD3 locus genetically modified to encode an extracellular domain of human CD3 protein, wherein the human CD3 protein is CD3ε, CD3δ, CD3γ, CD3ζ, or any combination thereof. In one embodiment, the endogenous non-human CD3 locus is genetically modified to encode an extracellular domain of human CD3ε, an extracellular domain of human CD3δ, and an extracellular domain of human CD3γ. In one embodiment, the endogenous non-human CD3 locus is genetically modified so as not to express functional extracellular domain(s) of the corresponding non-human protein(s). In one embodiment, the endogenous non-human CD3 locus further encodes transmembrane and cytoplasmic domains of corresponding endogenous non-human animal CD3 protein(s), wherein the animal expresses a chimeric CD3 protein on the surface of its T cells comprising the extracellular domain of the human CD3 protein and the transmembrane and cytoplasmic domains of the endogenous non-human animal CD3 protein. In one embodiment, a nucleic acid sequence(s) encoding the extracellular domain of the human CD3 in the non-human animal is operably linked to nucleic acid sequence(s) encoding transmembrane and cytoplasmic domains of the corresponding endogenous non-human animal CD3 protein(s). In a particular embodiment, the non-human animal comprises (a) at an endogenous CD3ε locus a nucleic acid sequence encoding an extracellular domain of a human CD3ε operably linked to a nucleic acid sequence encoding transmembrane and cytoplasmic domains of an endogenous non-human animal CD3ε, (b) at an endogenous CD3δ locus a nucleic acid sequence encoding an extracellular domain of a human CD3δ operably linked to a nucleic acid sequence encoding transmembrane and cytoplasmic domains of an endogenous non-human animal CD3δ, and (c) at an endogenous CD3γ locus a nucleic acid sequence encoding an extracellular domain of a human CD3γ operably linked to a nucleic acid sequence encoding transmembrane and cytoplasmic domains of an endogenous non-human animal CD3γ, wherein the non-human animal expresses chimeric CD3ε, CD3δ, and CD3γ proteins on the surface of its T cells. In some embodiments, the extracellular domain of the human CD3 protein in the non-human animal comprises the sequence selected from the group consisting of SEQ ID NO:33, SEQ ID NO:34, and SEQ ID NO:35. In some embodiments, the animal comprises extracellular domains of human CD3 proteins which comprise the sequences of SEQ ID NO:33, SEQ ID NO:34 and SEQ ID NO:35.

In some embodiments, the genetically modified non-human animal described herein comprises a nucleic acid sequence encoding an extracellular domain of human CD3 protein operably linked to a CD3 promoter. Thus, in some embodiments, the non-human animal described herein comprises a nucleic acid sequence encoding the extracellular domain of a human CD3ε, operably linked to a CD3 promoter, an extracellular domain of human CD3δ, operably linked to a CD3 promoter, and an extracellular domain of human CD3γ operably linked to a CD3 promoter. In one embodiment, the CD3 promoter is a non-human animal CD3 promoter. In one embodiment, the CD3 promoter is a human CD3 promoter. In one embodiment, the CD3 promoter is an endogenous non-human CD3 promoter.

In a particular embodiment, the non-human animal provided is a mammal. In one embodiment, the animal is a rodent. In one embodiment, the animal is a rat or a mouse.

In one embodiment, the animal is a mouse. Thus, in one embodiment, provided herein is a genetically modified mouse, wherein the mouse comprises (a) at an endogenous mouse CD3ϵ locus a nucleic acid sequence encoding an extracellular domain of a human CD3ϵ operably linked to a nucleic acid sequence encoding transmembrane and cytoplasmic domains of an endogenous mouse CD3ϵ, (b) at an endogenous mouse CD3δ locus a nucleic acid sequence encoding an extracellular domain of a human CD3δ operably linked to a nucleic acid sequence encoding transmembrane and cytoplasmic domains of an endogenous mouse CD3δ, and (c) at an endogenous mouse CD3γ locus a nucleic acid sequence encoding an extracellular domain of a human CD3γ operably linked to a nucleic acid sequence encoding transmembrane and cytoplasmic domains of an endogenous mouse CD3γ, and the mouse expresses humanized CD3ϵ, CD3δ, and CD3γ proteins on the surface of its T cells. In one embodiment, the amino acid sequence of the humanized CD3ϵ protein in said mouse is set forth in SEQ ID NO:24, the amino acid sequence of the humanized CD3δ protein is set forth in SEQ ID NO:25, and the amino acid sequence of the humanized CD3γ protein is set forth in SEQ ID NO:26. In one embodiment, the genetically modified mouse provided herein comprises a nucleic acid sequence encoding an extracellular domain of human CD3 operably linked to a mouse CD3 promoter. In one embodiment, the promoter is an endogenous mouse CD3 promoter. In another embodiment, the genetically modified mouse provided herein comprises a nucleic acid sequence encoding an extracellular domain of human CD3 operably linked to a human CD3 promoter. In one embodiment, the mouse displays similar CD4+ to CD8+ cell ratio in the thymus as compared to a mouse that is not genetically modified to express humanized CD3 proteins. In one embodiment, the mouse CD4+ to CD8+ T cell ratio in the thymus that is within 30%, within 25%, within 20%, within 15%, within 12%, within 10%, within 5%, or within 2% of the CD4+ to CD8+ cell ratio of a mouse that is not genetically modified to express humanized CD3 proteins. In one embodiment, the mouse displays similar T and B cell percentages in spleen, lymph nodes, and peripheral blood as a mouse that is not genetically modified to express humanized CD3 proteins. In one embodiment, the mouse displays similar numbers of circulating white blood cells, lymphocytes, monocytes, neutrophils, eosinophils, and basophils as a mouse that is not genetically modified to express humanized CD3 proteins.

Thus, in one aspect provided herein is a genetically modified mouse comprising at an endogenous mouse CD3 locus a nucleic acid sequence encoding an extracellular domain of human CD3 protein, wherein the human CD3 protein is selected from the group consisting of CD3ϵ, CD3δ, CD3γ, CD3ζ, and a combination thereof. In one embodiment, the mouse comprises extracellular domains of human CD3ϵ, CD3δ, and CD3γ. In one embodiment of the mouse, the extracellular domain of human CD3ϵ is set forth in SEQ ID NO:33, the extracellular domain of human CD3δ is set forth in SEQ ID NO:34, and the extracellular domain of human CD3γ is set forth in SEQ ID N0:35. In one embodiment, the mouse expresses a humanized CD3ϵ, a humanized CD3δ, and a humanized CD3γ. In one embodiment of the mouse, the humanized CD3ϵ is set forth in SEQ ID NO:24, the humanized CD3δ is set forth in SEQ ID NO:25, and the humanized CD3γ is set forth in SEQ ID NO:26. In one embodiment, the mouse further comprises mouse CD3ϵ, CD3δ, and CD3γ transmembrane and cytoplasmic domains. In one embodiment, the mouse further comprises endogenous mouse CD3ϵ, CD3δ, and CD3γ transmembrane and cytoplasmic domains.

In another aspect, provided herein is a method of making a genetically modified non-human animal expressing a humanized CD3 protein, comprising introducing a nucleic acid sequence encoding an extracellular domain of human CD3 protein, wherein the human CD3 protein is selected from the group consisting of CD3ϵ, CD3δ, CD3γ, CD3ζ, and a combination thereof into the genome of a cell of a non-human animal; and propagating the genetically modified non-human animal from the cell. In one embodiment of the method, the animal does not comprise a functional extracellular domain(s) of the corresponding non-human protein(s). In one embodiment of the method, the animal comprises at the endogenous CD3 locus a nucleic acid sequence encoding an extracellular domain of human CD3E, an extracellular domain of human CD3δ, and an extracellular domain of human CD3γ. In one embodiment of the method, the extracellular domain of human CD3ϵ is set forth in SEQ ID NO:33, the extracellular domain of human CD3δ is set forth in SEQ ID NO:34, and the extracellular domain of human CD3γ is set forth in SEQ ID NO:35. In one embodiment of the method, the animal does not comprise functional extracellular domain(s) of the corresponding non-human protein(s). In one particular embodiment, the method comprises replacing at the endogenous CD3 locus an extracellular domain of a non-human CD3 protein(s) with a corresponding extracellular domain of a human CD3 protein(s). In one embodiment of the method, the animal further comprises a nucleic acid sequence(s) encoding transmembrane and cytoplasmic domains of corresponding endogenous non-human animal CD3 protein(s). In one embodiment of the method, the non-human animal is a mouse and a replacement is at the endogenous mouse CD3 locus. In one embodiment of the method wherein the animal is a mouse, the mouse expresses a humanized CD3 protein selected from the group consisting of a humanized CD3ϵ set forth in SEQ ID NO: 24, a humanized CD3δ set forth in SEQ ID NO:25, a humanized CD3γ set forth in SEQ ID NO:26, and a combination thereof. In one embodiment of the method, the replacement is made in a single ES cell, and the single ES cell is introduced into the mouse embryo to make a mouse.

In yet another aspect, provided herein is a non-human animal model, e.g., a mouse model for testing a CD3-based bispecific antigen-binding protein, wherein the antigen-binding protein is capable of binding both CD3 and an antigen of interest, the mouse model comprising a mouse genetically modified to encode an extracellular domain of human CD3 protein, wherein the human CD3 protein is CD3ϵ, CD3δ, CD3γ, CD3ζ, or any combination thereof (e.g., two or more CD3 proteins) and comprising cell expressing or comprising the non-mouse antigen of interest. The non-human animal in the model can be any of the non-human animals described above or elsewhere herein. In one embodiment of the mouse model, the nucleic acid sequence(s) of the humanized CD3 protein(s) is located at the endogenous CD3 locus. In one embodiment of the mouse model, the antigen-binding protein has been introduced into said mouse. In one embodiment of the mouse model, the mouse expresses human CD3ϵ, CD3δ, and CD3γ extracellular domains. In one embodiment of the mouse model, the mouse further expresses mouse CD3ϵ, CD3δ, and CD3γ transmembrane and cytoplasmic domains.

In one embodiment of the mouse model, the mouse comprises a xenograft of a tumor expressing the antigen of interest. In one embodiment of the mouse model, the cell expressing or comprising the antigen of interest is a tumor cell. In one embodiment of the mouse model, the bispecific antigen-binding protein selected binds to both the humanized CD3 protein and the antigen of interest. In one embodiment of the mouse model, the antigen of interest is a human antigen. In one embodiment of the mouse model, the antigen binding protein is capable of binding a monkey CD3 protein. In one embodiment of the mouse model, the antigen of interest is a tumor associated antigen. In such an embodiment, the tumor associated antigen may be selected from the group consisting of ALK, BAGE proteins, BIRC5 (survivin), BIRC7, CA9, CALR, CCRS, CD19, CD20 (MS4A1), CD22, CD27, CD30, CD33, CD38, CD40, CD44, CD52, CD56, CD79, CDK4, CEACAM3, CEACAMS, CLEC12A, EGFR, EGFR variant III, ERBB2 (HER2), ERBB3, ERBB4, EPCAM, EPHA2, EPHA3, FCRLS, FLT3, FOLR1, GAGE proteins, GD2, GD3, GPNMB, GM3, GPR112, IL3RA, KIT, KRAS, LGRS, EBV-derived LMP2, L1CAM, MAGE proteins, MLANA, MSLN, MUC1, MUC2, MUC3, MUC4, MUC5, MUC16, MUM1, ANKRD30A, NY-ESO1 (CTAG1B), OX40, PAP, PAX3, PAXS, PLAC1, PRLR, PMEL, PRAME, PSMA (FOLH1), RAGE proteins, RET, RGSS, ROR1, SART1, SART3, SLAMF7, SLC39A6 (LIV1), STEAP1, STEAP2, TERT, TMPRSS2, Thompson-nouvelle antigen, TNFRSF17, TYR, UPK3A, VTCN1, WT1.

In another embodiment, the antigen of interest is an infectious disease associated antigen. In such an embodiment, the mouse may be infected with an infectious agent. In one such embodiment, the infectious disease associated antigen may be a viral antigen and the viral antigen is selected from the group consisting of HIV, hepatitis A, hepatitis B, hepatitis C, herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillomavirus, molluscum virus, poliovirus, rabies virus, JC virus, ebola virus, and arboviral encephalitis virus antigen. In another such embodiment, the infectious disease associated antigen may be a bacterial antigen and the bacterial antigen is selected from the group consisting of chlamydia, rickettsia, mycobacteria, staphylococci, streptococci, pneumonococci, meningococci, gonococci, klebsiella, proteus, serratia, pseudomonas, legionella, diphtheria, salmonella, bacilli, cholera, tetanus, botulism, anthrax, plague, leptospira, and Lyme disease bacterial antigen.

In one embodiment of the provided mouse model, the CD3-based antigen-binding protein is an antibody. In one embodiment, the CD3-based antigen-binding protein is a human or humanized antigen-binding protein. Such mouse model may allow testing for efficacy and/or toxicity of the antigen-binding protein in the mouse.

Also provided herein is a method of screening a drug candidate that target an antigen of interest comprising (a) introducing the antigen of interest into a genetically modified mouse comprising an endogenous non-human CD3 locus genetically modified to encode an extracellular domain of a human CD3 protein, wherein the human CD3 protein is CD3ε, CD3δ, CD3γ, CD3ζ, or any combination thereof as defined above or elsewhere herein, (b) contacting the mouse with a drug candidate of interest, wherein the drug candidate is directed against the human CD3 and the antigen of interest, and (c) determining if the drug candidate is efficacious in preventing, reducing or eliminating cells characterized by the presence or expression of the antigen of interest.

In one embodiment of the method, the genetically modified mouse comprises at the endogenous mouse CD3 locus a nucleic acid sequence encoding an extracellular domain of human CD3ε, an extracellular domain of human CD3δ, and an extracellular domain of human CD3γ. In one embodiment of the method, the mouse does not comprise a functional extracellular domain of the corresponding mouse protein(s). In one embodiment of the method, the mouse comprises a nucleic acid sequence(s) encoding transmembrane and cytoplasmic domains of corresponding endogenous mouse CD3 protein(s). In one embodiment of the method, the nucleic acid sequence(s) encoding the extracellular domain of the human CD3 is operably linked to the nucleic acid sequence(s) encoding transmembrane and cytoplasmic domains of the corresponding endogenous mouse CD3 protein(s). In one embodiment of the method, the extracellular domain of a human CD3ε is set forth in SEQ ID NO:33, the extracellular domain of a human CD3δ is set forth in SEQ ID NO:34, and the extracellular domain of a human CD3γ is set forth in SEQ ID NO:35. Thus, in one particular embodiment of the method, the mouse expresses a humanized CD3ε protein comprising an amino acid sequence set forth in SEQ ID NO:24, a humanized CD3δ protein comprising an amino acid sequence set forth in SEQ ID NO:25, and a humanized CD3γ protein comprising an amino acid sequence set forth in SEQ ID NO:26.

In a particular embodiment of the method of screening drug candidates described herein, the step of introducing the antigen of interest into the mouse described herein comprises expressing in the mouse the antigen of interest. In one embodiment, the step of expressing in the mouse the antigen of interest comprises genetically modifying the mouse to express the antigen of interest. In one embodiment, the step of introducing the antigen of interest comprises infecting the mouse with the antigen of interest. In one embodiment of the method, the step of introducing comprises introducing into said mouse a cell expressing the antigen of interest. In various embodiments of the method, the cell can be a tumor cell, a bacterial cell, or a cell infected with a virus. Thus, in some embodiments of the method, the mouse comprises and infection which is either a viral or bacterial infection. Thus, the antigen of interest can be an infectious disease associated antigen. In one embodiment, the antigen of interest is a viral antigen, and the viral antigen is selected from the group consisting of HIV, hepatitis A, hepatitis B, hepatitis C, herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillomavirus, molluscum virus, poliovirus, rabies virus, JC virus, ebola virus, and arboviral encephalitis virus antigen. In another embodiment, the antigen of interest is an infectious disease associated antigen, which is a bacterial antigen selected from the group consisting of chlamydia, rickettsia, mycobacteria, staphylococci, streptococci, pneumonococci, meningococci, gonococci, klebsiella, proteus, serratia, pseudomonas, legionella, diphtheria, salmonella, bacilli, cholera, tetanus, botulism, anthrax, plague, leptospira, and Lyme disease bacterial antigen.

In another embodiment of the method of screening drug candidates, the antigen of interest is a tumor associated antigen. In one embodiment of the method, the tumor associated antigen is selected from the group consisting of ALK, BAGE proteins, BIRC5 (survivin), BIRC7, CA9, CALR, CCR5, CD19, CD20 (MS4A1), CD22, CD27, CD30, CD33, CD38, CD40, CD44, CD52, CD56, CD79, CDK4, CEACAM3, CEACAM5, CLEC12A, EGFR, EGFR variant III, ERBB2 (HER2), ERBB3, ERBB4, EPCAM, EPHA2, EPHA3, FCRL5, FLT3, FOLR1, GAGE proteins, GD2, GD3, GPNMB, GM3, GPR112, IL3RA, KIT, KRAS, LGRS, EBV-derived LMP2, L1CAM, MAGE proteins, MLANA, MSLN, MUC1, MUC2, MUC3, MUC4, MUC5, MUC16, MUM1, ANKRD30A, NY-ESO1 (CTAG1B), OX40, PAP, PAX3, PAM, PLAC1, PRLR, PMEL, PRAME, PSMA (FOLH1), RAGE proteins, RET, RGSS, ROR1, SART1, SART3, SLAMF7, SLC39A6 (LIV1), STEAP1, STEAP2, TERT, TMPRSS2, Thompson-nouvelle antigen, TNFRSF17, TYR, UPK3A, VTCN1, WT1.

In some embodiments of the method of screening drug candidates, the mouse is an immunocompetent mouse. In some embodiments of the method described herein, the antigen of interest is a human antigen of interest.

In some embodiments of the method, the drug candidate is an antibody. In some embodiments, the drug candidate is an antigen-binding protein. In some embodiments, the drug candidate is a bispecific antibody or a bispecific antigen binding protein. In some embodiments, the bispecific antigen binding protein is capable of binding both human CD3 protein and the antigen of interest. In one embodiment, the drug candidate is capable of recognizing a monkey CD3 protein.

In some embodiments of the method of screening drug candidates, the drug candidate is capable of reducing, eliminating, or preventing tumor growth as compared to an agent that does not target the antigen of interest. In some embodiments of such method the step of determining if the drug candidate is efficacious in preventing, reducing or eliminating cells characterized by the presence or expression of the antigen of interest comprises a tumor volume assay or a T cell mediated tumor cell killing assay.

In other embodiments, the drug candidate is capable of reducing, eliminating, or preventing bacterial or viral infection as compared to an agent that does not target the antigen of interest. In some such embodiments, the step of determining if the drug candidate is efficacious in preventing, reducing or eliminating cells characterized by the presence or expression of the antigen of interest comprises the measurement of viral or bacterial titers.

In yet other embodiments, provided herein is a non-human animal model, e.g., a mouse model, for testing safety, efficacy, and pharmacokinetics of combination drug therapies wherein the combination therapy includes a drug, e.g., an antigen-binding protein, that binds a human CD3 molecule. Such combination therapies are aimed at targeting specific tumors, infections, or other diseases described herein which can benefit from the recruitment and/or activation of T cells.

BRIEF DESCRIPTION OF THE DRAWINGS

FIGS. 2A and B are the schematic representation (not to scale) of the humanized CD3γδε large targeting vector. FIG. 2A depicts the large targeting vector before the selection cassette (Neo) deletion, with human CD3E, CD3D, and CD3G sequence knock-in locations indicated. A, B, C, D, E, F, and G indicate location of the junction nucleic acid sequences represented in Table 1. FIG. 2B depicts the large targeting vector after deletion of the selection cassette (Neo); similarly to FIG. 2A, locations of the human CD3E, CD3D, and CD3G are indicated. A-B, C, D, E, F, and G are locations of the junction nucleic acid sequences represented in Tables 1 and 3.

FIG. 3 depicts the amino acid sequences of the humanized CD3 proteins in the humanized CD3γδε mice. The CD3 protein sequences of human origin are underlined.

FIG. 4 depicts alignments between mouse and human CD3e, CD3d, and CD3g sequences. The 5' and 3' ends of the human sequences that were introduced into mouse CD3 loci are marked with * and **, respectively.

FIG. 5B bottom row is data depicting percentages of T and B cells in the spleen of indicated animals.

FIGS. 6A-B are a demonstration of viral LCMV titers in the spleens of either wild type control or humanized CD3γδε mice in mice infected with LCMV Clone 13 (FIG. 6A), or LCMV clone 13 following prior LCMV Armstrong clone infection (FIG. 6B).

FIG. 8A demonstrates transient T and B cell depletion in blood of mice treated with anti-CD3 antibodies; either T cell depletion on day 1 for each antibody indicated (left figure), or T and B cell depletion and recovery over 14 days for each antibody tested (middle and right figures).

FIG. 10 is a table summarizing various properties of the humanized CD3 mouse model.

DETAILED DESCRIPTION

Definitions

Figure 1:
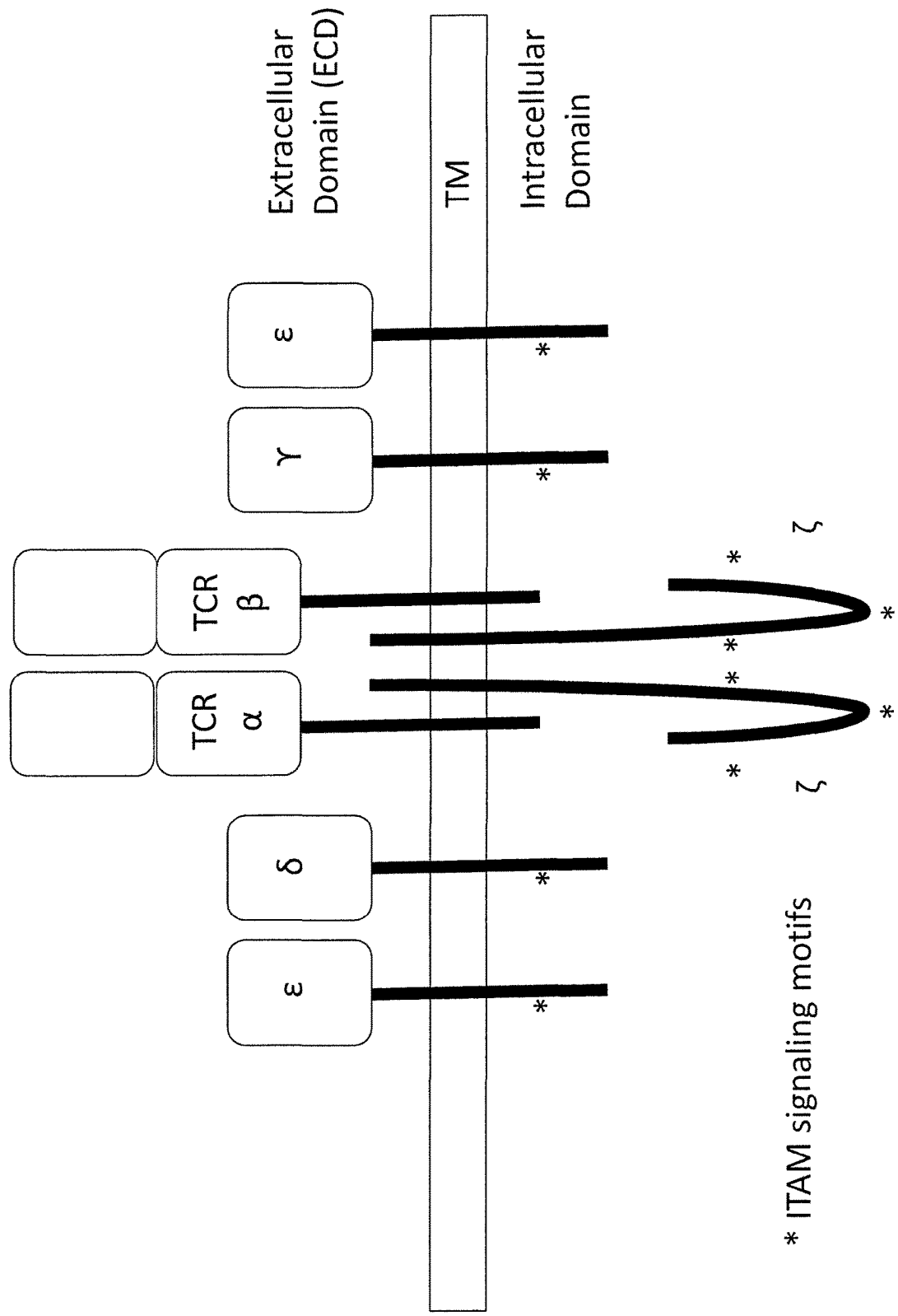
FIG. 1 depicts the structure of T cell receptor complex. The complex comprises two CD3ε subunits, one CD3δ subunit, one CD3γ subunit, and two CD3ζ subunits, complexed with the TCRαβ heterodimer on a T cell surface. Asterisks indicate the locations of the ITAM motifs.

The present invention provides genetically modified non-human animals, e.g., rodents, e.g., mice or rats, which express humanized CD3 proteins, e.g., humanized CD3ε, CD3δ, CD3γ, and/or CD3ζ proteins. The present invention also relates to genetically modified non-human animals that comprise in their genome, e.g., in their germline, genetically modified CD3 loci encoding humanized CD3 proteins, e.g., chimeric human/mouse CD3 proteins. Also provided are embryos, cells, and tissues comprising the same, methods of making the same, as well as methods of using the same. Unless defined otherwise, all terms and phrases used herein include the meanings that the terms and phrases have attained in the art, unless the contrary is clearly indicated or clearly apparent from the context in which the term or phrase is used.

"CD3," as used herein, includes an antigen which is expressed on T cells as part of the multimolecular T cell receptor (TCR) complex; the multimolecular TCR complex formed from association of homodimers and/or heterodimers comprising one or more of the following receptor chains: CD3-epsilon (ε), CD3-delta (δ), CD3-zeta (ζC), and CD3-gamma (γ) (See FIG. 1). Sequences and GenBank Accession Numbers of human and mouse CD3-delta, CD3-zeta, and CD3-gamma are presented in Table 4 below. Throughout the application, ε or epsilon can also be written as E, δ or delta can also be written as D, ζ or zeta can also be written as Z, and γ or gamma can also be written as G.

As used herein, "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

The term "conservative," when used to describe a conservative amino acid substitution, includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of CD3 proteins to play a role in T cell receptor assembly and signaling. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database, Science 256: 1443-45), hereby incorporated by reference. In some embodiments, the substitution is a moderately conservative substitution wherein the substitution has a nonnegative value in the PAM250 log-likelihood matrix.

Thus, encompassed by the invention is a genetically modified non-human animal, e.g., rodent, e.g., mouse or rat, expressing a humanized CD3 protein(s) comprising conservative amino acid substitutions in the amino acid sequence described herein.

One skilled in the art would understand that in addition to the nucleic acid residues encoding humanized CD3 proteins described herein, due to the degeneracy of the genetic code, other nucleic acids may encode the polypeptides of the invention. Therefore, in addition to a genetically modified non-human animal that comprises in its genome nucleotide sequences encoding humanized CD3 proteins described herein, a non-human animal that comprises in its genome nucleotide sequences that differ from those described herein due to the degeneracy of the genetic code are also provided.

The term "identity" when used in connection with sequence includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences. In various embodiments, identity is determined by comparing the sequence of a mature protein from its N-terminal to its C-terminal. In various embodiments, when comparing a humanized sequence to a human sequence, the human portion of the humanized sequence (hut not the non-human portion) is used in making a comparison for the purpose of ascertaining a level of identity between a human sequence and a humanized sequence.

The term "operably linked" includes a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. In addition, various portions of the humanized protein of the invention may be operably linked to retain proper folding, processing, targeting, expression, and other functional properties of the protein in the cell. Unless stated otherwise, various domains of the humanized protein of the invention are operably linked to each other. Operable linkage of a human extracellular domain of a CD3 protein and nonhuman transmembrane and cytoplasmic domains can be achieved by expressing these components as a contiguous fusion protein from a nucleic acid coding sequence.

The term "replacement" in reference to gene replacement includes placing exogenous genetic material at an endogenous genetic locus, thereby replacing all or a portion of the endogenous gene with an orthologous or homologous nucleic acid sequence. In one instance, an endogenous non-human gene or fragment thereof is replaced with a corresponding human gene or fragment thereof. For example, DNA encoding the extracellular domain of a mouse or other non-human CD3 protein can be replaced with DNA encoding the extracellular domain of the corresponding human protein A corresponding human gene or fragment thereof is a human gene or fragment that is an ortholog of, a homolog of, or is substantially identical or the same in structure and/or function, as the endogenous non-human gene or fragment thereof that is replaced. As demonstrated in the Examples below, nucleotide sequences encoding endogenous non-human CD3 extracellular domains were replaced by nucleotide sequences corresponding to human CD3 extracellular domains.

"Functional" as used herein, e.g., in reference to a functional protein, includes a protein that retains at least one biological activity normally associated with the native protein. For example, in some embodiments of the invention, a replacement at an endogenous locus (e.g., replacement at endogenous non-human CD3 loci) results in a locus that fails to express a functional endogenous protein.

The term "locus" as in CD3 locus includes the genomic DNA comprising a CD3 coding region. The different CD3 genes CD3ε, CD3δ, CD3γ map proximate to one another the same chromosome. Thus depending on the context, reference to an endogenous CD3 locus may refer to a locus including some or all of these coding regions or an individual coding region. For example, if only one of the human CD3s, such as CD3ε is introduced into a non-human animal, then the nucleic acid encoding that CD3 preferably modifies the locus of the corresponding non-human CD3. If several human CD3's are introduced into a non-human animal such as CD3ε, CD3δ, CD3γ, then the modified endogenous locus includes the coding regions of each of CD3ε, CD3δ, and CD3γ. A CD3 locus can also refer to the locus of CD3ζ, which occupies a different chromosome than CD3ε, CD3δ, and CD3γ. If human CD3ζ is introduced together with any of human CD3ε, CD3δ, or CD3γ, then two or more CD3 loci can be modified on different chromosomes. Other sequences may be included in the CD3 locus that have been introduced for the purposes of genetic manipulation, e.g., selection cassettes, restriction sites, etc.

The term "germline" in reference to an immunoglobulin nucleic acid sequence includes a nucleic acid sequence that can be passed to progeny.

The phrase "immunoglobulin molecule" includes two immunoglobulin heavy chains and two immunoglobulin light chains. The heavy chains may be identical or different, and the light chains may be identical or different.

The term "antibody", as used herein, includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains, $C_H1$, $C_H2$ and $C_H3$. Each light chain comprises a light chain variable domain and a light chain constant region ($C_L$). The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3).

The term "high affinity" antibody refers to an antibody that has a $K_D$ with respect to its target epitope about of $10^{-9}$ M or lower (e.g., about $1\times10^{-9}$ M, $1\times10^{-10}$ M, $1\times10^{-11}$ M, or about $1\times10^{-12}$ M).

The phrase "bispecific antibody" includes an antibody capable of selectively binding two epitopes. Bispecific antibodies generally comprise two arms, each binding a different epitope (e.g., two heavy chains with different specificities)—either on two different molecules (e.g., different epitopes on two different immunogens) or on the same molecule (e.g., different epitopes on the same immunogen). If a bispecific antibody is capable of selectively binding two different epitopes (a first epitope and a second epitope), the affinity of the first antibody arm for the first epitope will generally be at least one to two or three or four or more orders of magnitude lower than the affinity of the first antibody arm for the second epitope, and vice versa. Epitopes specifically bound by the bispecific antibody can be on the same or a different target (e.g., on the same or a different protein). Exemplary bispecific antibodies include those with a first antibody arm specific for a tumor antigen and a second antibody arm specific for a cytotoxic marker, e.g., an Fc receptor (e.g., FcγRI, FcγRII, FcγRIII, etc.) or a T cell marker (e.g., CD3, CD28, etc.). In one embodiment of the present invention, one arm of the bispecific antibody is specific for CD3. Further, a bispecific antibody with a first arm specific for a tumor antigen and a second arm specific for a toxin can be paired so as to deliver a toxin (e.g., saporin, vinca alkaloid, etc.) to a tumor cell. Other exemplary bispecific antibodies include those with a first arm specific for an activating receptor (e.g., B cell receptor, FcγRI, FcγRIIA, FcγRIIIA, FcγRI, T cell receptor, etc.) and a second arm specific for an inhibitory receptor (e.g., FcγRIIB, CD5, CD22, CD72, CD300a, etc.). Such bispecific antibodies can be constructed for therapeutic conditions associated with cell activation (e.g., allergy and asthma). Bispecific antibodies can be made, for example, by combining heavy chains that recognize different epitopes of the same immunogen. For example, nucleic acid sequences encoding heavy chain variable sequences that recognize different epitopes of the same immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a $C_H1$ domain, a hinge, a $C_H2$ domain, and a $C_H3$ domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding of one or both of the heavy chains to one or both epitopes. Similarly, the phrase "multispecific antibody" includes an antibody capable of selectively binding multiple epitopes (e.g., two, three, four epitopes).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule. A CDR can be encoded by, for example, a germline sequence or a rearranged or unrearranged sequence, and, for example, by a naive or a mature B cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The phrase "functional fragment" includes fragments of antigen-binding proteins such as antibodies that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. A heavy chain variable domain is encoded by a variable region gene sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found on the website for the International Immunogenetics Information System (IMGT database).

The phrase "light chain" includes an immunoglobulin light chain sequence from any organism, and unless otherwise specified includes human kappa and lambda light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region. A light chain variable domain is encoded by a light chain variable region gene sequence, which generally comprises $V_L$ and $J_L$ segments, derived from a repertoire of V and J segments present in the germline. Sequences, locations and nomenclature for V and J light chain segments for various organisms can be found on the website for the International Immunogenetics Information System (IMGT database). Light chains include those, e.g., that do not selectively bind any epitopes recognized by antigen-binding protein (e.g., antibody) in which they appear. Light chains also include those that bind and recognize, or assist the heavy chain with binding and recognizing, one or more epitopes selectively bound by the antigen-binding protein (e.g., an antibody) in which they appear.

The term "antigen-binding protein" as used herein includes antibodies and various naturally produced and engineered molecules capable of binding the antigen of interest. Such include, e.g., domain-specific antibodies, single domain antibodies (e.g., derived from camelids and fish, etc.), domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), shark variable IgNAR domains, etc. Antigen-binding protein may also include antigen-binding fragments such as, e.g., (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), etc.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell). In some embodiments, the cell is an ES cell.

A humanized CD3 protein means a CD3 protein in which, in one embodiment, an extracellular domain is of human sequence. The transmembrane and cytoplasmic domains can also be human but are preferably non-human endogenous sequences. A CD3 protein including sequences from different species, particularly a human extracellular domain, and non-human transmembrane and cytoplasmic domains, can also be referred to as a chimeric CD3 protein.

Genetically Modified Humanized CD3 Animals

In various embodiments, the present invention provides genetically modified non-human animals (e.g., rodents, e.g., mice or rats) that comprise in their genome (e.g., in their germline genome) a nucleic acid sequence encoding a humanized CD3 protein (e.g., a humanized CD3ε, CD3γ, CD3δ, or combination thereof). In one embodiment, the present invention provides genetically modified non-human animals (e.g., rodents, e.g., mice or rats) that comprise in their genome nucleotide sequences encoding humanized CD3δ, humanized CD3γ, and humanized CD3ε proteins. Thus, in some embodiments of the invention, the mouse expresses a humanized CD3γδε complex on the surface of its T cells such that the humanized CD3γδε forms a complex with the T cell receptor expressed on the same T cell.

CD3 molecule is commonly a target of agents that are aimed at modulating T cell immunity, and several anti-CD3 antibodies have been developed for that purpose (e.g., muromonab-CD3 or OKT3). Anti-CD3 antibodies such as OKT3 are used as immunosuppressive agents (e.g., in transplant rejection) but are also studied for their therapeutic potential in autoimmune diseases (e.g., Crohn's disease, type 1 diabetes, ulcerative colitis, etc.).

Additionally, CD3 molecules are also being studied as targets for bispecific agents, e.g., bispecific antibodies, because of the ability of anti-CD3 bispecific antibodies to recruit T cells to a target cell, e.g., a cell that expresses a particular antigen of interest. Exemplary anti-CD3 bispecific antibodies are described in U.S. Patent Application Publication No. 2014/0088295, and US. Patent Application Publication No. 2015/0266966, both incorporated herein by reference.

During preclinical drug development stage, candidate agents are typically studied based on their efficacy, toxicity, and other pharmacokinetic and pharmacodynamics properties. Candidate agents, such as antibodies, typically target a human antigen—as the end goal of investigation is to develop a human therapy. Many preclinical studies are conducted in large animals such as primates as their physiology and drug metabolism are most similar to humans. Several antibodies developed to CD3 (e.g., OKT3) are known not to cross-react to non-human CD3, particularly to primate CD3. To conduct effective preclinical investigations relating to efficacy, toxicity, and other parameters of a drug candidate, first, the drug candidate must be determined to recognize primate CD3 molecule.

However, a separate factor complicating development of anti-CD3 therapy is that large primates such as chimpanzees are endangered and in many countries studies in chimpanzees are prohibited; while studies in other primates, e.g., cynomolgus monkeys (Macaca fascicularis), may raise ethical concerns. For example, for all of the above reasons, to date there is no effective primate model of human tumors. Thus, any preliminary data on a specific therapeutic candidate that can be obtained in a smaller animal model, such as a rodent, e.g., a mouse, can be helpful in determining further progress of preclinical investigations in large primates.

Preclinical studies in small animal models, such as mice, have traditionally been conducted using drug surrogates. For example, when a clinical candidate targeting a specific human antigen is in development, some preclinical data is generated in a mouse using a molecule, e.g., an antigen binding protein or an antibody, which specifically targets a mouse homolog of the antigen of interest. Information about efficacy, various dosing regimens, toxicity and side effects, and other aspects of drug administration is gathered from such drug surrogate studies. However, such findings are limited because it is not the actual drug that is in development or its human target that is being studied.

Thus, the most useful small animal model to conduct preliminary preclinical studies is a non-human animal, e.g., a rodent, that expresses a human or humanized CD3 protein, and allows the testing of anti-CD3 drug candidates that also cross-react with cynomolgus monkey CD3, allowing for subsequent primate preclinical studies. The present invention provides such an intricate animal model.

Thus, provided herein is a genetically modified non-human animal comprising in its genome a nucleic acid sequence(s) encoding an extracellular domain of a human CD3 protein. In some embodiments of the invention, the CD3 protein is selected from the group consisting of CD3γ, CD3δ, CD3ε, CD3ζ, and a combination thereof. In some embodiments, the CD3 protein is selected from the group consisting of CD3γ, CD3δ, CD3ε, and a combination thereof. In some embodiments, the CD3 protein comprises CD3γ, CD3δ, and CD3ε polypeptide chains. Thus, in some embodiments, the genetically modified non-human animal comprises in its genome a nucleic acid sequence(s) encoding an extracellular domain of a human a CD3γ, an extracellular domain of a human CD3δ, and an extracellular domain of a human CD3ε. In some such embodiments, the extracellular domains of human CD3γ, CD3δ, and CD3ε may be encoded by a single nucleic acid. In some embodiments, the extracellular domains of human CD3γ, CD3δ, and CD3ε are encoded by separate nucleic acids.

In some embodiments, the non-human animal described herein retains endogenous nonhuman CD3 promoter(s) and/or regulatory elements (e.g., endogenous nonhuman CD3γ, CD3δ, and/or CD3ε promoters and/or regulatory elements). In other embodiments, the non-human animal comprises human CD3 promoter(s) and regulatory elements.

Although it has been postulated that the majority of antibodies generated against CD3 recognize CD3ε epitopes (see, Tunnacliffe et al. (1989) International Immunology, 1(5):546-50), there are a number of agents that may either recognize other CD3 subunits (e.g., CD3γ or CD3δ) or require assembly of the CD3 complex for binding. Thus, the genetically modified non-human animal that comprises in its genome a nucleic acid sequence(s) encoding an extracellular domain of a human a CD3γ, an extracellular domain of a human CD3δ, and an extracellular domain of a human CD3ε, provides an advantage since it can accommodate an agent that would bind any of the CD3 subunits or the CD3 complex.

Exemplary CD3 proteins are presented in the alignment in FIG. 4. A mouse CD3ε protein sequence can be found in GenBank Accession Number NP_031674 and SEQ ID NO:27, while a human CD3s protein sequence can be found in GenBank Accession Number NP_000724 and SEQ ID NO:28. A mouse CD3δ protein sequence can be found in GenBank Accession Number NP_038515 and SEQ ID NO:29, while a human CDS protein sequence can be found in GenBank Accession Number NP_000723 and SEQ ID NO:30. A mouse CD3γ protein sequence can be found in GenBank Accession Number NP_033980 and SEQ ID NO:31, while a human CD3γ protein sequence can be found in GenBank Accession Number NP_000064 and SEQ ID NO:32.

In some embodiments of the invention, the nucleic acid sequence(s) encoding an extracellular domain of a human CD3, e.g., an extracellular domain of a human a CD3γ, human CD3δ, and human CD3ε, are located at an endogenous non-human CD3 locus. In other words, such a nucleic acid modifies the endogenous CD3 locus to encode the human CD3 polypeptide. In some embodiments of the invention, the non-human animal does not comprise a functional extracellular domain of the corresponding non-human CD3 protein because of genetic modification of the endogenous locus so that the functional extracellular domain is not expressed. In some embodiments of the invention, the nucleic acid sequence(s) encoding an extracellular domain of a human CD3 replaces corresponding nucleic acid sequence(s) encoding endogenous non-human CD3. Thus, in some embodiments, the nucleic acid sequence encoding the extracellular domain of a human CD3γ replaces the nucleic acid sequence encoding the extracellular domain of endogenous non-human CD3γ, the nucleic acid sequence encoding the extracellular domain of a human CD3δ replaces the nucleic acid sequence encoding the extracellular domain of endogenous non-human CD3δ, and the nucleic acid sequence encoding the extracellular domain of a human CD3γ replaces the nucleic acid sequence encoding the extracellular domain of endogenous non-human CD3ε. In some embodiments, the replacement does not comprise the replacement of a nucleic acid sequence encoding endogenous signal sequence. In another embodiment the replacement comprises the replacement of the nucleic acid sequence encoding endogenous signal sequence with the nucleic acid sequence encoding a human signal sequence.

In some aspects of the invention, the extracellular domain comprises the region of the protein(s) that is not a transmembrane or a cytoplasmic domain, e.g., the region of the protein that appears on the surface of the cell and that, in part, when assembled in a complex interacts with the extracellular domains of other components of TCR signaling complex, e.g., TCR alpha and beta extracellular domains. In various embodiments described herein, extracellular domain refers to the domain of the protein expressed on the cell surface and, unless indicated otherwise, does not include the signal sequence which is typically proteolytically cleaved prior to sell surface expression. In some embodiments of the invention, the extracellular domain of CD3ε comprises amino acids 17-130 of the amino acid sequence set forth in SEQ ID NO:24 (set forth separately as SEQ ID NO:33). In some such embodiments, the animal comprises the nucleic acid sequence encoding an endogenous CD3ε signal sequence, e.g., signal sequence at amino acids 1-16 of SEQ ID NO:24. In other embodiments of the invention, the animal comprises the nucleic acid sequence encoding a human CD3ε signal sequence. In some embodiments of the invention, the extracellular domain of CD3δ comprises amino acids 19-105 of the amino acid sequence set forth in SEQ ID NO:25 (set forth separately as SEQ ID NO:34). In some such embodiments, the animal comprises the nucleic acid sequence encoding an endogenous CD3δ signal sequence, e.g., signal sequence at amino acids 1-18 of SEQ ID NO:25. In other embodiments of the invention, the animal comprises the nucleic acid sequence encoding a human CD3δ signal sequence. In some embodiments, the extracellular domain of CD3γ comprises amino acids 20-116 of the amino acid sequence set forth in SEQ ID NO:26 (set forth separately as SEQ ID NO:35). In some such embodiments, the animal comprises the nucleic acid sequence encoding endogenous CD3γ signal sequence, e.g., signal sequence at amino acids 1-19 of SEQ ID NO:26. In other embodiments of the invention, the animal comprises the nucleic acid sequence encoding a human CD3γ signal sequence.

In some aspects of the invention, the non-human animal comprises a nucleic acid sequence encoding transmembrane and cytoplasmic domains of endogenous CD3 protein, e.g., corresponding endogenous CD3 protein. Thus, in one embodiment, the non-human animal comprises a nucleic acid sequence encoding the extracellular domain of the human CD3 protein operably linked to the nucleic acid sequence encoding transmembrane and cytoplasmic domains of the corresponding endogenous non-human CD3 protein so that a chimeric protein comprising the extracellular domain of the human CD3 protein and the transmembrane and cytoplasmic domains of the corresponding endogenous non-human CD3 protein is expressed. Thus, in one aspect, the animal comprises at an endogenous CD3 locus a nucleic acid sequence(s) encoding an extracellular domain of a human CD3 protein operably linked to a nucleic acid sequence(s) encoding transmembrane and cytoplasmic domains of an endogenous non-human CD3. In one embodiment, the animal comprises at an endogenous CD3ε locus a nucleic acid sequence encoding an extracellular domain of a human CD3ε operably linked to a nucleic acid sequence encoding transmembrane and cytoplasmic domains of an endogenous non-human animal CD3ε, at an endogenous CD3δ locus a nucleic acid sequence encoding an extracellular domain of a human CD3δ operably linked to a nucleic acid sequence encoding transmembrane and cytoplasmic domains of an endogenous non-human animal CD3δ, and at an endogenous CD3γ locus a nucleic acid sequence encoding an extracellular domain of a human CD3γ operably linked to a nucleic acid sequence encoding transmembrane and cytoplasmic domains of an endogenous non-human animal CD3γ. Use of chimeric CD3 proteins with a human extracellular domain and endogenous transmembrane and cytoplasmic domains allows for interaction of drugs with specificity for human CD3 but may also allow to recapitulate the interaction with the endogenous T-cell receptor and its signal transduction components compared with a fully human CD3 protein.

In some aspects of the invention, the non-human animal expresses extracellular domains of human CD3 protein. In some aspects, the non-human animal expresses an extracellular domain of human CD3ε set forth in SEQ ID NO:33. In some aspects, the non-human animal expresses an extracellular domain of human CD3δ set forth in SEQ ID NO:34. In some aspects, the non-human animal expresses an extracellular domain of human CD3γ set forth in SEQ ID NO:35.

In some embodiments of the invention, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In one embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the genetically modified non-human animal is a rodent. In one embodiment, the genetically modified non-human animal is a rat or a mouse. In one embodiment, the animal is a mouse. Thus, in one embodiment, the genetically modified animal is a mouse and the mouse comprises at an endogenous mouse CD3 locus a nucleotide sequence encoding an extracellular domain of a human CD3 protein. In one embodiment, the mouse comprises a nucleic acid sequence encoding an extracellular domain of a human CD3ε, a nucleic acid sequence encoding an extracellular domain of a human CD3δ, and a nucleic acid sequence encoding an extracellular domain of a human CD3γ. In some embodiments of the invention, the extracellular domain of the human CD3ε comprises the sequence set forth in SEQ ID NO:33, the extracellular domain of the human CD3δ comprises the sequence set forth in SEQ ID NO:34, and the extracellular domain of the human CD3γ comprises the sequence set forth in SEQ ID NO:35. In some embodiments, the mouse comprises the sequence(s) encoding endogenous mouse CD3 signal sequence(s). In other embodiments, the mouse comprises the sequence(s) encoding human CD3 signal sequence(s).

In some embodiments of the invention, the mouse of the invention expresses humanized CD3 protein(s). In one embodiment, the mouse expresses humanized CD3ε, humanized CD3δ, and humanized CD3γ proteins. In some embodiments of the invention, the mouse expresses a human CD3ε extracellular domain and endogenous mouse CD3ε transmembrane and cytoplasmic domains, a human CD3δ extracellular domain and endogenous mouse CD3δ transmembrane and cytoplasmic domains, and a human CD3γ extracellular domain and endogenous mouse CD3γ transmembrane and cytoplasmic domains. In some such embodiments, the mouse expresses humanized CD3 proteins wherein the humanized CD3 proteins are humanized CD3ε set forth in SEQ ID NO:24, humanized CD3δ set forth in SEQ ID NO:25, and humanized CD3γ set forth in SEQ ID NO:26.

In some aspects of the invention, the genetically engineered mouse is an immunocompetent mouse. In some embodiments of the invention, the introduction of humanized CD3 protein(s) does not affect the mouse's immune system function. In some embodiments of the invention, the mouse comprises normal T and B cell ratio. In some embodiments of the invention, the mouse is capable of mounting a normal response to mouse infection. In some aspects, the mouse displays similar CD4+ to CD8+ cell ratio in the thymus as compared to a wild type mouse, e.g., a mouse that has not been genetically modified to express humanized CD3 protein(s). In some embodiments of the invention, the CD4+ to CD8+ cell ratio in the thymus of the mouse is within 30%, e.g., within 20%, e.g., within 15%, e.g., within 12%, e.g., within 10%, e.g., within 5%, e.g., within 2%, of the CD4+ to CD8+ cell ratio of a mouse that is not genetically modified to express humanized CD3 protein(s). In some aspects, the mouse displays similar T and B cell percentages in the spleen, lymph nodes, and peripheral blood as a wild type mouse, e.g., a mouse that is not genetically modified to express humanized CD3 protein(s). In some aspects, the mouse displays similar numbers of circulating white blood cells, lymphocytes, monocytes, neutrophils, eosinophils, and basophils as a wild type mouse, e.g., a mouse that is not genetically modified to express humanized CD3 protein(s).

Also provided herein are methods of making the genetically modified non-human animal described herein. In some embodiments, the method of making a genetically modified non-human animal wherein the animal expresses a humanized CD3 protein comprises introducing at an endogenous non-human animal CD3 locus a nucleic acid sequence encoding an extracellular domain of a human CD3 protein, wherein the human CD3 protein is selected from the group consisting of CD3ε, CD3δ, CD3γ, CD3δ, and a combination thereof. If multiple human CD3 proteins are introduced, they can be introduced together on a single nucleic acid (as in the present Examples) or separately. If the latter, a single cell line (e.g., ES cell line) can undergo successive modifications until modified to include nucleic acids encoding each of the desired human CD3ε. In one embodiment the animal does not comprise a functional extracellular domain of the corresponding non-human CD3 protein(s). In one aspect, the animal comprises at an endogenous non-human CD3 locus a nucleic acid sequence encoding an extracellular domain of human CD3ε, an extracellular domain of human CD3δ, and an extracellular domain of human CD3γ. In some embodiments, the extracellular domain of a human CD3ε is set forth in SEQ ID NO:33, the extracellular domain of a human CD3δ is set forth in SEQ ID NO: 34, and the extracellular domain of a human CD3γ is set forth in SEQ ID NO:35. In one embodiment, the animal does not comprise a functional extracellular domain of the corresponding non-human CD3 protein(s).

In some embodiments, the method of making a genetically modified non-human animal of the invention comprises replacing at the endogenous CD3 locus a nucleotide sequence encoding the extracellular domain of a non-human CD3 protein(s) with a nucleotide sequence encoding an extracellular domain of a corresponding human CD3 protein(s). In one embodiment, the animal retains transmembrane and cytoplasmic domains of the non-human CD3 protein(s). In some embodiments, the replacement results in a chimeric protein(s) comprising an extracellular domain of a human CD3 protein(s) and transmembrane and cytoplasmic domains of corresponding endogenous non-human CD3 protein(s).

Nucleic acid(s) encoding human CD3 protein(s) are typically introduced into a cell, and a non-human animal is propagated from the cell. In some embodiments, the replacement method utilizes a targeting construct made using VELOCIGENE® technology, introducing the construct into ES cells, and introducing targeted ES cell clones into a mouse embryo using VELOCIMOUSE® technology, as described in the Examples.

In one embodiment, wherein the method comprises the replacement of the nucleotide sequence encoding the extracellular domain of endogenous non-human CD3ε with the nucleotide sequence encoding the extracellular domain of a human CD3ε protein, the method comprises a replacement of partial sequence of endogenous mouse coding exons 2 to 4 of mouse CD3ε gene with partial sequence of human coding exons 2 to 5 of human CD3ε gene. In one embodiment, wherein the method comprises the replacement of the nucleotide sequence encoding the extracellular domain of endogenous non-human CD3δ with the nucleotide sequence encoding the extracellular domain of a human CD3δ, the method comprises a replacement of partial sequence of endogenous mouse coding exons 2 to 3 of mouse CD3δ with the partial sequence of human coding exons 2 to 3 of human CD3δ gene. In one embodiment, wherein the method comprises a replacement of the nucleotide sequence encoding the extracellular domain of endogenous non-human CD3γ with the nucleotide sequence encoding the extracellular domain of human CD3γ, the method comprises replacement of partial sequence of mouse coding exons 2 to 4 of mouse CD3γ with the partial sequence of human coding exons 2 to 4 of human CD3γ gene. In one embodiment of the invention, the replacement comprises the replacement of sequence of CD3δ, CD3δ, and CD3γ. In such an embodiment, the replacement may be accomplished by creating a large targeting vector that incorporates the sequential genetic modification in all three loci and then introducing the large targeting vector into mouse ES cells to make a mouse, e.g., as described in Example 1.

Thus, in one embodiment, provided herein is a large targeting vector for making a genetically modified animal of the invention. In one embodiment, the large targeting vector comprises 5' and 3' mouse homology arms; a DNA fragment comprising the CD3ε gene which comprises a replacement of partial sequence of mouse CD3ε coding exons 2 to 4 with partial sequence of human CD3ε coding exons 2 to 5; a DNA fragment comprising the CD3δ gene which comprises a replacement of partial sequence of mouse CD3δ coding exons 2 to 3 with partial sequence of human CD3δ coding exons 2 to 3; a DNA fragment comprising the CD3γ gene which comprises a replacement of partial sequence of mouse CD3γ coding exons 2 to 4 with partial sequence of human CD3γ coding exons 2 to 4; and a selection cassette.

A selection cassette is a nucleotide sequence inserted into a targeting construct to facilitate selection of cells (e.g., bacterial cells, ES cells) that have integrated the construct of interest. A number of suitable selection cassettes are known in the art (Neo, Hyg, Pur, CM, SPEC, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art. A selection cassette may be located anywhere in the construct outside the coding region. In one embodiment, the selection cassette is inserted upstream of human CD3e inserted sequence.

Upon completion of gene targeting, ES cells or genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCR (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

Heterozygotes resulting from the above methods can be bred to generate homozygotes.

In one aspect, a method for making a chimeric human/non-human CD3 molecule is provided, comprising expressing in a single cell a chimeric CD3 protein from a nucleotide construct as described herein. In one embodiment, the nucleotide construct is a viral vector; in a specific embodiment, the viral vector is a lentiviral vector. In one embodiment, the cell is selected from a CHO, COS, 293, HeLa, and a retinal cell expressing a viral nucleic acid sequence (e.g., a PERC.6™ cell).

In one aspect, a cell that expresses a chimeric human/non-human CD3 protein is provided. In one embodiment, the cell comprises an expression vector comprising a chimeric CD3 sequence as described herein. In one embodiment, the cell is selected from CHO, COS, 293, HeLa, and a retinal cell expressing a viral nucleic acid sequence (e.g., a PERC.6™ cell).

A chimeric CD3 molecule made by a non-human animal as described herein is also provided, wherein, in one embodiment, the chimeric CD3 molecule comprises an amino acid sequence of all or substantially all of an extracellular domain of a human CD3 protein, and at least transmembrane and cytoplasmic domains from a non-human CD3 protein, e.g., mouse CD3 protein.

In addition to a genetically engineered non-human animal, a non-human embryo (e.g., a rodent, e.g., a mouse or a rat embryo) is also provided, wherein the embryo comprises a donor ES cell that is derived from a non-human animal (e.g., a rodent, e.g., a mouse or a rat) as described herein. In one aspect, the embryo comprises an ES donor cell that comprises the chimeric CD3 gene, and host embryo cells.

Also provided is a tissue, wherein the tissue is derived from a non-human animal (e.g., a rodent, e.g., a mouse or a rat) as described herein, and expresses the chimeric CD3 protein.

In addition, a non-human cell isolated from a non-human animal as described herein is provided. In one embodiment, the cell is an ES cell. In one embodiment, the cell is a T cell. In one embodiment, the cell is a $CD8_+$ T cell. In another embodiment, the cell is a CD4+ T cell.

In some embodiments, also provided herein are genetic loci comprising the nucleic acid sequences that encoding the humanized CD3 protein(s) described herein.

Mouse Model for Testing Human Therapies

In some aspects, provided herein is a mouse model for testing CD3-targeted ("anti-CD3") therapeutic agents. In some embodiments, provided herein is a mouse model for testing anti-CD3 antigen-binding proteins. In some embodiments, provided herein is a mouse model for testing anti-CD3 antibodies. In some such embodiments, provided is a mouse model for testing anti-CD3 multispecific, e.g. bispecific antigen-binding proteins or anti-CD3 bispecific antibodies. As such, an anti-CD3 multispecific antigen-binding protein, e.g. an anti-CD3 bispecific antigen-binding protein, targets or specifically binds said humanized CD3 protein and at least one other antigen of interest. In various aspects, the mouse model for testing anti-CD3 bispecific antigen-binding proteins wherein the antigen-binding protein is capable of binding both CD3 and the antigen of interest comprises a nucleic acid sequence encoding a humanized CD3 protein, wherein the humanized CD3 protein is selected from the group consisting of CD3ε, CD3δ, CD3γ, CD3ζ, and a combination thereof, and a cell expressing or comprising the antigen of interest. In one embodiment, the mouse comprises a T cell expressing said humanized CD3 protein(s).

In an embodiment, the testing of the monospecific or bispecific antigen-binding protein involves performing an assay or a study that allows determination of the effect of the antigen-binding protein on the T cell expressing said humanized CD3 protein. In another embodiment, the testing of the bispecific antigen-binding protein involves performing an assay or a study that allows determination of the effect of the antigen-binding protein on both the T cell expressing said humanized CD3 protein and the cell expressing or comprising the antigen of interest, or the interaction between said CD3-expressing T cell and the cell expressing or comprising the antigen of interest. In one embodiment, the testing of the monospecific or bispecific antigen-binding protein involves performing an assay or a study that allows determination of the effect of the T cell expressing said humanized CD3 protein on the cell expressing or comprising said antigen of interest. In one embodiment, such assay measures, e.g., the number of cells expressing the antigen of interest, immune response, cellular interactions, cellular cytotoxicity, cytokine release, cellular activation, cell proliferation, tumor growth or regression, changes in pathology, or the like. Various assays include but are not limited to measurements of complement-directed cytotoxicity (CDC), antibody-dependent cytotoxicity (ADCC), antibody-dependent cellular phagocytosis (ADCP), PBMC proliferation, CD69 activation, histological tissue analysis, analysis of tissue and cellular biomarkers (e.g., cells or tissue may be extracted from the mouse for the purpose of the assays, or analyzed by radiography, MRI, PET, SPECT, BLI, and fluorescence-based imaging modalities).

In some embodiments of the invention, in such a mouse model, the antigen of interest has been introduced into said mouse. The antigen of interest may be introduced by several methods known to those skilled in the art. Some nonlimiting methods include transgenesis, injection, infection, tissue or cell transplantation. The antigen of interest or a fragment thereof (e.g., a fragment that is recognized by the antigen-binding protein being tested) can be targeted to, or expressed by, particular cell types. In some embodiments, the antigen of interest is a humanized antigen of interest encoded by the mouse genome.

The antigen of interest may be a membrane-bound protein such that it is expressed only on cell surface. Alternatively, the antigen of interest or a fragment thereof (e.g., a fragment that is recognized by the antigen-binding protein being tested) may be displayed on the cell surface complexed with another protein or moiety. Some cell-surface antigens may associate with other proteins as co-receptor complexes, or bind or have affinity to extracellular molecules. Thus, the mouse model may be utilized to test bispecific antigen-binding molecules that interact with T cells in various cell systems.

In one embodiment, the mouse model expresses human CD3ε, CD3δ, CD3γ extracellular domains. In one embodiment, the mouse expresses mouse transmembrane and cytoplasmic domain of CD3ε, CD3δ, and CD3γ; an in one embodiment, the transmembrane and cytoplasmic domains are endogenous mouse domains. In one embodiment, the mouse model expresses CD3ε, CD3δ, and CD3γ, each comprising a human extracellular domain and mouse, e.g., endogenous mouse, transmembrane and cytoplasmic domains.

In various embodiment of the invention, the antigen-binding protein binds both CD3 and the antigen of interest in the mouse model. In one embodiment, the antigen of interest is a human antigen. In one embodiment, the antigen of interest is a primate antigen, e.g., a cynomolgus monkey antigen. In one embodiment, the antigen-binding protein is capable of binding the same antigen of interest of both human and monkey origin. In one embodiment, the antigen-binding protein is capable of binding both human and monkey CD3.

In one embodiment, the mouse model comprises a xenograft of a tumor expressing the antigen of interest. In one embodiment, the cell expressing or comprising the antigen of interest in said mouse is an immortalized cell, such as a tumor cell. Thus, the mouse model is utilized to test the activity of anti-CD3 bispecific antigen-binding proteins in blocking or affecting the tumor cell expressing the antigen of interest.

Thus, in the embodiment of the invention, wherein the cell expressing or comprising the antigen of interest is a tumor cell, the antigen of interest may be a tumor-associated antigen (TAA). Various tumor antigens are listed in the database of T cell defined tumor antigens (van der Bruggen P, Stroobant V, Vigneron N, Van den Eynde B. Peptide database: T cell-defined tumor antigens. Cancer Immun 2013). Exemplary tumor associated antigens include but are not limited to ALK, BAGE proteins, BIRC5 (survivin), BIRC7, CA9, CALR, CCRS, CD19, CD20 (MS4A1), CD22, CD27, CD30, CD33, CD38, CD40, CD44, CD52, CD56, CD79, CDK4, CEACAM3, CEACAM5, CLEC12A, EGFR, EGFR variant Ill, ERBB2 (HER2), ERBB3, ERBB4, EPCAM, EPHA2, EPHA3, FCRLS, FLT3, FOLR1, GAGE proteins, GD2, GD3, GPNMB, GM3, GPR112, IL3RA, KIT, KRAS, LGR5, EBV-derived LMP2, L1CAM, MAGE proteins, MLANA, MSLN, MUC1, MUC2, MUC3, MUC4, MUC5, MUC16, MUM1, ANKRD30A, NY-ESO1 (CTAG1B), OX40, PAP, PAX3, PAXS, PLAC1, PRLR, PMEL, PRAME, PSMA (FOLH1), RAGE proteins, RET, RGSS, ROR1, SART1, SART3, SLAMF7, SLC39A6 (LIV1), STEAP1, STEAP2, TERT, TMPRSS2, Thompson-nouvelle antigen, TNFRSF17, TYR, UPK3A, VTCN1, WT1. In one example, as described in Example 3 herein, the antigen of interest may be CD20, e.g., human or humanized CD20.

In another embodiment of the invention, the mouse model is used to determine if a candidate bispecific antigen-binding protein is capable of blocking or affecting an antigen of interest which is an infectious disease associated antigen. In one embodiment of the invention, the mouse is infected with an infectious agent. In one embodiment of the invention, the infectious disease associated antigen is a viral antigen. In one aspect, the viral antigen is selected from the group consisting of HIV, hepatitis A, hepatitis B, hepatitis C, herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillomavirus, molluscum virus, poliovirus, rabies virus, JC virus, ebola virus, and arboviral encephalitis virus antigen.

In another embodiment of the invention, wherein the antigen of interest is an infectious disease associated antigen, the antigen of interest is a bacterial antigen. In some aspects of the invention, the bacterial antigen is selected from the group consisting of chlamydia, rickettsia, mycobacteria, staphylococci, streptococci, pneumonococci, meningococci, gonococci, klebsiella, proteus, serratia, pseudomonas, legionella, diphtheria, salmonella, bacilli, cholera, tetanus, botulism, anthrax, plague, leptospira, and Lyme disease bacterial antigen.

In some aspects of the invention, the CD3-based bispecific antigen binding protein is a human CD3 based antigen binding protein. In one embodiment, the antigen binding protein is an antibody, e.g., a human antibody, or an antigen-binding fragment thereof.

In some embodiments of the invention, the mouse model is an immunocompetent mouse model. In some embodiments of the invention, the mouse model allows for testing of efficacy and/or toxicity of an antigen-binding protein of interest. The measures of efficacy will depend on the antigen of interest being targeted by the bispecific agent. In some embodiments, the measure of efficacy is T cell killing of the cell expressing the antigen. In other embodiments, the measure of efficacy is neutralization of the virus. In other embodiment, the measure of efficacy may be viability of the animal. In yet another embodiment, the measure of efficacy may be elimination of cells expressing the antigen of interest, proliferation of T cells, production of cytokines (e.g., IFNg, TNFa, IL-1, IL-2, IL-10, IL4, IL-6, granzyme, perform, etc.)

In some embodiments of the invention, the toxicity in the animal may be measured as an adverse event in the animal, e.g., change in body weight, appetite, digestive changes, changes in blood cell counts, splenomegaly, histological changes of the organs, change in liver enzyme function, changes in urinalysis, organ toxicity, hemorrhage, dehydration, loss of fur and scruffiness, or other signs of morbidity. One measure may be determination of antigen-binding protein cross-reactivity with irrelevant antigens, which, in one embodiment, can be detected by organ histology, specifically detection of antigen-binding protein in tissues or cell types that are not known to express the antigen of interest.

Use of Genetically Modified Non-Human Animals

The invention also provides various methods of using the genetically modified non-human animals described herein.

In one embodiment, provided herein is a method of screening therapeutic drug candidates that target an antigen of interest comprising (a) providing or receiving a genetically modified mouse comprising at its endogenous mouse CD3 locus a nucleic acid sequence encoding an extracellular domain of a human CD3 protein selected from the group consisting of CD3ϵ, CD3δ, CD3γ, CD3ζ, and a combination thereof, (b) introducing into said genetically modified mouse an antigen of interest, (c) contacting said mouse with a drug candidate of interest, wherein the drug candidate is directed against the human CD3 and the antigen of interest, and (d) determining if the drug candidate is efficacious in preventing, reducing or eliminating cells characterized by the presence or expression of the antigen of interest. In various embodiments, the mouse expresses a functional humanized CD3 protein on the surface of its T cells. In one embodiment of the method, the genetically modified mouse comprises at the endogenous mouse CD3 locus a nucleic acid sequence encoding an extracellular domain of human CD3ϵ, an extracellular domain of human CD3δ, and an extracellular domain of human CD3γ. In one embodiment of the method described herein, the mouse does not comprise the nucleic acid sequence encoding a functional extracellular domain of the corresponding mouse protein. In some embodiments of the method, the extracellular domain(s) of the human CD3 protein(s) is operably linked to the transmembrane and cytoplasmic domain(s) of the corresponding endogenous mouse CD3 protein(s). In various such embodiments of the methods, the extracellular domain of a human CD3δ is set forth in SEQ ID NO:33, the extracellular domain of a human CD3δ is set forth in SEQ ID NO:34, and the extracellular domain of a human CD3γ is set forth as SEQ ID NO:35. In various embodiment of the methods described here, the mouse may express a humanized CD3ϵ protein set forth in SEQ ID NO:24, a humanized CD3δ protein set forth in SEQ ID NO:25, and a humanized CD3γ set forth in SEQ ID NO:26.

In various embodiments of the method described herein, introduction of the antigen of interest into the genetically modified mouse described herein may be accomplished by any methods known to those skilled in the art, which may include, without limitation, transgenesis, injection, infection, tissue or cell transplantation. As such, introduction may be achieved by expressing in the mouse the antigen of interest, which can comprise genetically modifying said mouse to express the antigen of interest. Alternatively, introduction may comprise introduction into said mouse a cell expressing the antigen of interest, e.g., as in cell or tissue transplantation. Introduction may also comprise infecting said mouse with the antigen of interest, e.g., as in bacterial or viral infection. In one embodiment, the antigen of interest may be a human antigen of interest. In another embodiment, it may be a bacterial or a viral antigen of interest.

The antigen of interest may be a tumor-associated antigen, as described in detail above. The antigen may also be an infectious disease associated antigen, e.g., a bacterial or a viral antigen, as described in detail above.

In various embodiments of the methods of screening a therapeutic drug candidate, the drug candidate may be an antigen-binding protein, e.g., an antibody, e.g., a bispecific antibody. In various aspects, such drug candidate is capable of binding both human CD3 and the antigen of interest. The antigen of interest may be a human antigen. The antigen of interest may also be a primate, e.g., a monkey, antigen. Thus, the drug candidate used for screening may be capable of binding both a human antigen and a corresponding primate antigen, in addition to binding human CD3. The drug candidate may also be capable of binding primate, e.g., monkey, CD3. Thus, the drug candidate may be capable of binding both human and primate, e.g., monkey, CD3; and also, in one embodiment, be capable of binding a human antigen of interest. In another embodiment, the antigen of interest may be a bacterial or a viral antigen, and the drug candidate may be capable of binding both the human and primate, e.g., monkey, CD3 and the bacterial or viral antigen of interest.

In some aspects, the therapeutic candidate is an antibody, which is a human antibody. In other aspects, it may be a humanized antibody. For example, the therapeutic candidate may be an antibody generated in VELOCIMMUNE® mice (U.S. Pat. No. 8,502,018, incorporated herein by reference); thus, the initial antibody candidate may comprise a human variable region and a mouse constant region. The mouse constant region of the antibody candidate may be reengineered to be of human origin by expressing the human variable region selected in VELOCIMMUNE® mice in operable linkage with a human constant region.

In various embodiments of the methods described herein, the therapeutic candidate is capable of reducing, eliminating, or preventing a disease. In one embodiment, the disease is a tumor, and the therapeutic candidate is capable of reducing, eliminating, or preventing tumor growth as compared to an agent that does not target the antigen of interest. In such an embodiment of the method, determination whether the drug candidate is efficacious in preventing, reducing or eliminating cells characterized by the presence or expression of the antigen of interest can be performed using a tumor volume assay, a tumor cell killing assay, induction of apoptotic markers in tumors, reduction in blood vessel growth in tumors, infiltration of immune cells into tumors, etc. In another embodiment, the disease is an infectious disease, and a therapeutic candidate is capable reducing, eliminating, or preventing a bacterial or a viral infection as compared to an agent that does not target the antigen of interest. In such an embodiment of the method, determination whether the drug candidate is efficacious in preventing, reducing or eliminating cells characterized by the presence or expression of the antigen of interest can be performed using a measure of bacterial or viral titers, induction of apoptotic markers in infected cells, etc.

Other methods of use of the humanized CD3 mice of the present invention are also provided. For example, the non-human animal, e.g., a humanized CD3 mouse, described herein may be used to study the mechanism of drug action. Prior to the development of the present animal, it was difficult to study the mechanism of drug action as such studies are not typically conducted in humans and primates, and often require an immunocompetent animal model. Understanding drug action mechanism can lead to development of better antibodies. In various embodiments of the invention, the humanized CD3 mouse is an immunocompetent mouse. For example, the humanized CD3 mouse of the invention, which comprises a healthy normal immune system with intact development and complete complement of all immune cell types and intact immune signaling pathways, can be used to study the effects of various therapeutic candidates on specific cell types, cytokines, chemokines, etc. The mouse can then be used to answer mechanistic questions relating to drug candidate function.

In addition, the humanized CD3 mice can be used in methods that involve testing the effect of bispecific anti-CD3 drug candidates on tumor grafts. Previously developed mouse models were immunocompromised mouse models to allow for proper human tumor engraftment. Humanized CD3 mouse is fully immunocompetent and allows introduction and growth of tumor cells expressing the antigen of interest, so full affect on the immune response can be studied, included but not limited to answering mechanistic questions, early toxicity questions, early efficacy questions, etc.

In yet other embodiments, the humanized CD3 mouse can be used to study the effects of combination drug therapies in animal models, specifically combination drug therapies, e.g., where one drug is an antigen-binding protein that binds CD3 and another drug is an agent that has previously been approved for a particular indication. Specific questions related to the dosing of the drugs and its effects can be addressed in an animal model prior to any human trials.

EXAMPLES

The following examples are provided so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1

Construction of Humanized CD3 Locus

Example 1.1

Construction of Humanized CD3 γδε

The mouse CD3 locus was humanized by construction of unique targeting vectors from human and mouse bacterial artificial chromosomes (BAC) DNA using VELOCIGENE® technology (see, e.g., U.S. Pat. No. 6,586,251 and Valenzuela et al. (2003) High-throughput engineering of the mouse genome couple with high-resolution expression analysis. Nat. Biotech. 21(6): 652-659, both incorporated herein by reference). DNA from mouse BAC bMQ-425K11 was modified by homologous recombination to replace the genomic DNA encoding portions of mouse CD3ε, CD3δ, and CD3γ genes (mouse CD3 genes located within close proximity to one another on chromosome 9) with corresponding portions of CD3ε, CD3δ, and CD3γ genes derived from human BAC RP11-414G21 (human CD3 genes are located within close proximity to one another on chromosome 11), respectively.

Specifically, to generate humanized CD3γδε mice, the mouse BAC was first modified by replacing 714 bp of mouse Cd3d sequence (corresponding to partial sequence of mouse coding exons 2-3 of Cd3d gene) with 939 bp of human CD3D sequence (corresponding to partial sequence of human coding exons 2-3 of CD3D gene) in a single targeting event using a targeting vector comprising a Spec cassette using mouse homology arms.

Mouse BAC comprising a replacement of partial sequence of mouse coding exons 2-3 of CD3d gene with corresponding human sequence was subsequently modified by replacement of 1,738 bp of mouse Cd3g sequence (corresponding to partial sequence of mouse coding exons 2-4 of Cd3g gene) with 1,639 bp of human CD3G sequence (corresponding to partial sequence of human coding exons 2-4 of CD3G gene) also in a single targeting event using another Spec cassette-containing vector and mouse homology arms.

Finally, the BAC comprising the replacement of mouse CD3d and CD3g genes with corresponding human genes was further modified by replacing 6,213 bp mouse CD3e sequence with 6,817 bp of human sequence (corresponding to replacement of partial sequence of mouse coding exons 2 to 4 of mouse CD3e gene with partial sequence of human coding exons 2 to 5 of human CD3E gene). A 4,996 bp floxed neomycin cassette was inserted upstream of human CD3E sequence knock-in.

The resulting humanized large targeting vector for insertion into ES cells is depicted in FIG. 2A, with A, B, C, D, E, F, and G indicating various mouse/human or mouse/NEO cassette or human/NEO cassette junctions. The sequences at the junctions are depicted in Table 1 below.

TABLE 1

Junctional Sequences of the Large Targeting Vector

| Sequence designation in FIG. 1 | Junction | Sequence | SEQ ID NO: |
|---|---|---|---|
| A | 5' mouse Cd3e/ XhoI/(loxP) cassette | CGACTTTCTTGACTTCTATTTGTTA AACACTGTGCATTCACATCGAATGC TAGAAGTTTCCTCGTCCCGCTTCCT CCTGAATTGCCTGGGATCCTCTGCT TGATGCCCTGTAGGAAACGTCCTTT CCTGTGGTATAGAAATGACTG/CTC GAG/ATAACTTCGTATAATGTATGC TATACGAAGTTATATGCATGGCCTC CGCGCCGGGTTTTGGCGCCTCCCGC | 1 |
| B | 3' cassette (loxP)IceUl//human CD3E | TGTATCTTATCATGTCTGGAATAAC TTCGTATAATGTATGCTATACGAAG TTATGCTAGTAACTATAACGGTCCT AAGGTAGCGAGCTAGC//CTTCCAC AGACACCAATGTTCAAAATGGAGGC TTGGGGGCAAAATTCTTTTGCTATG TCTCTAGTCGTCCAAAAAATGGTCC TAACTTTTTCTGACTCCTGCTTGTC AAAAATTGTGGGCTCATAGTTAATGC | 2 |
| C | 3' human CD3E/ mouse Cd3e | AGGGGAGAATGGCCTTCATGCACTCC CTCCTCACCTCCAGCGCCTTGTGTTT TCCTTGCTTAGTGATTTCCCCTCTCC CCACCCCACCCCCCACAGTGTGTGAG AACTGCATGGAGATGGATGTGATGTC GGTG/GCCATAATCATCATTGTTGAC ATCTGTATCACTCTGGGCTTGCTGAT GGTCATTTATTACTGGAGCAAGAATA GGAAGGCCAAGGCCAAGCCT | 3 |
| D | 3' mouse Cd3d/ human CD3D | GAAAGAGAGAGTCTTTCTGCTAACTA ACCCCCAGAAGGCCTTCCGGTCTCAT GTCCTGCAAAGCAGTAGACGCCCAAA GCCAGGAGCAGAGTTGCGATGAGGTC AATGAAGATGACACC/AGCCACGGTG GCTGGATCCAGCTCCACACAGCTCTG GCACACTGTGGGGAAGGGAGGAGAG AGGAGAGGTTGAGAGCCTTTAAGATC AGGGAACCATCCT | 4 |
| E | 5' human CD3D/SgrDI/mouse Cd3d | CAAGAGAGACAGAAGTCACAAGAAAA AGCCTTCAGAAAGTTCCCCACCAACT GCAGGGGTCAAGGGGGACATGAGGAT GCCATTCAAG/CGTCGACG/AGCGTA GGCAGCTTATTGCTCTGCATACTTAC AGACCATTTGTGTAGTAAGGGACATG ATGCCGAGTGAAAGGGGCAGGAGCAA CCAGAGGGAGATTTCAGGAAGTTCTC CAGGGACTCGAGGTTCGTGA | 5 |
| F | 5' mouse Cd3g/AsisI/human CD3G | GAAGCCCCACCCAGAAAGGTAGGACAA AGATCATAGTCATATTTACTTCATCCA GGAGAGAAACACAGACACAGCCATTGC CTTGGCCATCATCTCTCTCCATCTTGA CCTCACGTGATCATG/GCGATCGC/GA GTGATTTAGTCTACAATCCGGAAAACT AAGTATAGATACTACCATTTTCATGGA TTTGGATCTTTCTTCATCTTGGCCTCA AATAACCATG | 6 |
| G | 3' human CD3G/mouse Cd3g | GCATTATTGCAGACAGGCAGGAGAAAA CGAACCAGGAAAAACAACTTTCGCAAC CTGAAGGTTTGTCTCTCCTTTTCCCTA CAGTGTGTCAGAACTGCATTGAACTAA ATGCAGCCACCATATCT/GGCTTTATC TTCGCTGAGGTCATCAGCATCTTCTTC CTTGCTCTTGGTGTATATCTCATTGCG GGACAGGATGGACAATACCCTGTCTTA A | 7 |

The targeted BAC DNA was used to electroporate mouse ES cells comprising a deletion in mouse CD3 locus to create modified ES cells for generating mice that express humanized CD3ε, CD3δ, and CD3γ on the surface of their T cells. ES cells containing insertions of human CD3ε, CD3δ, and CD3γ sequences were identified by a quantitative TAQMAN™ assay (see, e.g., Lie and Petropoulos, 1998. Curr. Opin. Biotechnology 9:43-48, incorporated herein by reference). Specific primer sets and probes were designed for detecting insertion of human sequences (gain-of-allele, GOA) and deletion of mouse sequences (loss-of-allele, LOA). Table 2 identifies the names and locations of each of primers/probe sets used in the quantitative PCR assays.

Nature Biotech. 25(491-99). VELOCIMICE® (FO mice fully derived from the donor ES cell) independently bearing a humanized CD3 genes were identified by genotyping using a modification of allele assay (see above) that detects the presence of the unique human CD3 gene sequences.

The selection cassette may be removed by methods known by the skilled artisan. For example, ES cells bearing the humanized CD3 locus may be transfected with a construct that expresses Cre in order to remove floxed cassette. The selection cassette may optionally be removed by breeding to mice that express Cre recombinase. Optionally, the selection cassette is retained in the mice. The mouse/human

TABLE 2

Primers/Probe Pairs Used for Genotyping

| Gene | Sequence Name | Assay | Fwd Primer | Probe (BHQ) | Rev Primer |
|---|---|---|---|---|---|
| Mouse Cd3e | 968 mTU | LOA | CCTCTGCCATG TAGGTTTGTG TAC (SEQ ID NO: 9) | TGCCGTGATGT TTGTTCAATGA CCAAA (SEQ ID NO: 10) | GTTCTGAG AAAGGCGT TCTTAAGTG (SEQ ID NO: 11) |
| Mouse Cd3g | 7164 mTD | LOA | CCAGGCGTACT TGCTGTTCTG (SEQ ID NO: 12) | TGGGCTTACCAT CCAGGACGA (SEQ ID NO: 13) | GCTACTCTTC CCACAAACTG CTTAG (SEQ ID NO: 14) |
| Human CD3E | 7170 hTU | GOA | CCAGCAGTAAG TTCCACTGTTC TAG (SEQ ID NO: 15) | TGTAGAAATGG CTGTGACCCAGCA (SEQ ID NO: 16) | GGGCTGTGTT GCAGTATGAC (SEQ ID NO: 17) |
| Human CD3D | 928 hTU | GOA | ACCGTGCAAGT TCATTATCGAAG (SEQ ID NO: 18) | ACGTGCTTCCTG AACCCTTTGGGT (SEQ ID NO: 19) | TCTCACATCCA GAAGCCCTATC (SEQ ID NO: 20) |
| Human CD3G | 7164 hTD | GOA | CGAGGGATGTA TCAGTGTAAAG GA (SEQ ID NO: 21) | CACAGAACAAGT CAAAACCACTCC AAGTG (SEQ ID NO: 22) | GCTCACCAGAA CAGCAAATACTG (SEQ ID NO: 23) |

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) FO generation mice that are essentially fully derived from the donor gene-targeted ES cells allowing immediate phenotypic analyses junction of the humanized CD3E allele after selection cassette removal (depicted as A-B in FIG. 2B), is presented in Table 3 below. The remaining junction sequences are the same as in the targeting vector and are presented in Table 1 above.

TABLE 3

Junctional Sequences of the Humanized Allele

| Sequence designation in FIG. 1B | Junction | Sequence | SEQ ID NO: |
|---|---|---|---|
| A-B | 5'mouse Cd3e/XhoI/Lox/IceUI// human CD3E | CGACTTTCTTGACTTCTATTTGTTAAA CACTGTGCATTCACATCGAATGCTAGA AGTTTCCTCGTCCCGCTTCCTCCTGAA TTGCCTGGGATCCTCTGCTTGATGCCC TGTAGGAAACGTCCTTTCCTGTGGTAT AGAAATGACTGCTCGAG/ATAACTTC GTATAATGTATGCTATACGAAGTTAT/GCTAGTAACTATAACGGTCCTAAGGTA GCGAGCTAGC//CTTCCACAGACACCA ATGTTCAAAATGGAGGCTTGGGGCAA AATTCTTTTGCTATGTCTCTAGTCGTC CAAAAAATGGTCCTAACTTTTTCTGAC TCCTGCTTGTCAAAAATTGTGGGCTCA TAGTTAATGC | 8 |

The sequence of the resulting humanized CD3ε, CD3δ, and CD3γ proteins is depicted in FIG. 3 and included in the sequence listing. Additionally, alignment of mouse-human sequences and junctions at the 5' and 3' of inserted human sequence are shown in FIG. 4 as * and **, respectively. GenBank Protein Accession Numbers for CD3ε, CD3δ, and CD3γ proteins are summarized below in Table 4.

TABLE 4

GenBank Protein Accession Numbers

| Protein Name | Mouse Accession # (SEQ ID NO) | Human Accession # (SEQ ID NO) |
| --- | --- | --- |
| CD3ε | NP_031674 (SEQ ID NO: 27) | NP_000724 (SEQ ID NO: 28) |
| CD3δ | NP_038515 (SEQ ID NO: 29) | NP_000723 (isoform A) (SEQ ID NO: 30) |
| CD3γ | NP_033980 (SEQ ID NO: 31) | NP_000064 (SEQ ID NO: 32) |

Example 2

Characterization of Humanized CD3 Mice

Example 2.1

Immune Cell Development in Humanized CD3 Mice

Immune cell development in the thymus and periphery of human CD3thy mice was assessed using fluorescence-activated cell sorting (FACS) analysis and differential cell counting. Thymus, spleen and lymph nodes were harvested from cohorts of wildtype (WT, no human CD3γδε), heterozygous (Het, one hCD3γδε allele) and homozygous (Ho, two hCD3γδε alleles) mice. Peripheral blood was obtained by cardiac puncture or retro-orbital bleed into EDTA coated Microtainer tubes (BD). Single cell suspensions were prepared from the spleen, LN and thymus using mechanical disruption, and red blood cells were removed from the spleen, thymus and whole blood by lysis with AKC Lysis buffer. Cells were incubated for 10 minutes at room temperature with purified antibodies to CD16/CD32 (FcBlock) to block non-specific binding via Fc receptors, and then incubated for 30 minutes at 4° C. with a cocktail of directly conjugated antibodies to T and B cell markers. Cells were washed twice with cold PBS containing 1% BSA, resuspended in buffer and analyzed by flow cytometry on a FACSCanto II™ flow cytometer (BD Biosciences). Thymocytes were identified first by forward and side scatter gating, and then by gating on the B220− population. In the periphery, T cells were identified as CD45+/TCRb+/B220−, and B cells were identified as CD45+/TCRb−/B220+. Absolute counts were obtained on a Hemavet 950FS Hematology Analyzer.

Figure 5A:
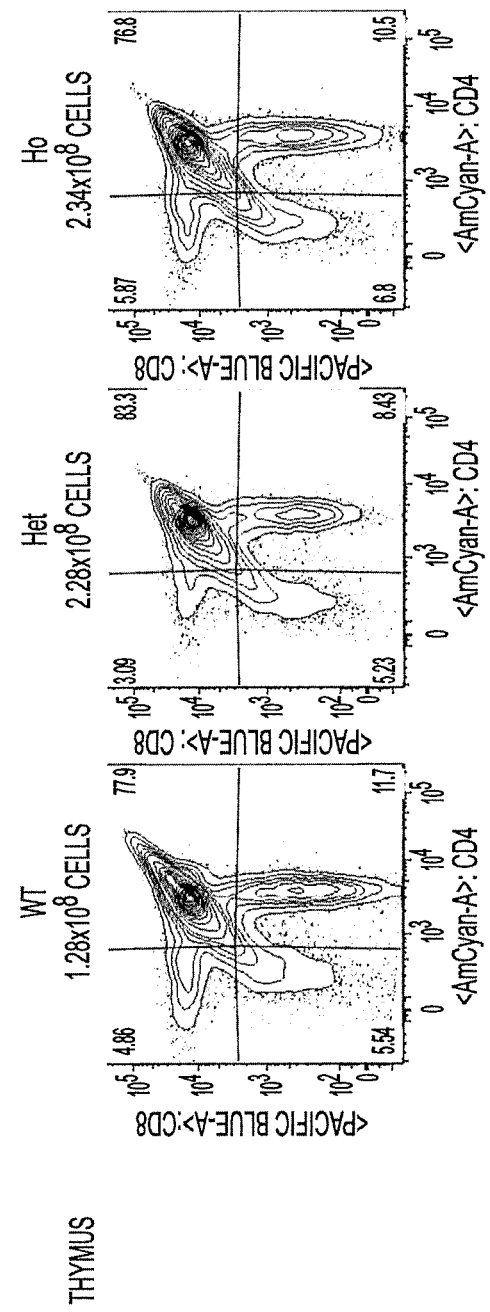
FIG. 5A, top row, is a FACs analysis plot demonstrating normal distribution of CD4+ and CD8+ thymocytes in wild type (WT), heterozygous humanized CD3γδε (HET), or homozygous humanized CD3γδε (HO) mice.
Figure 5B:
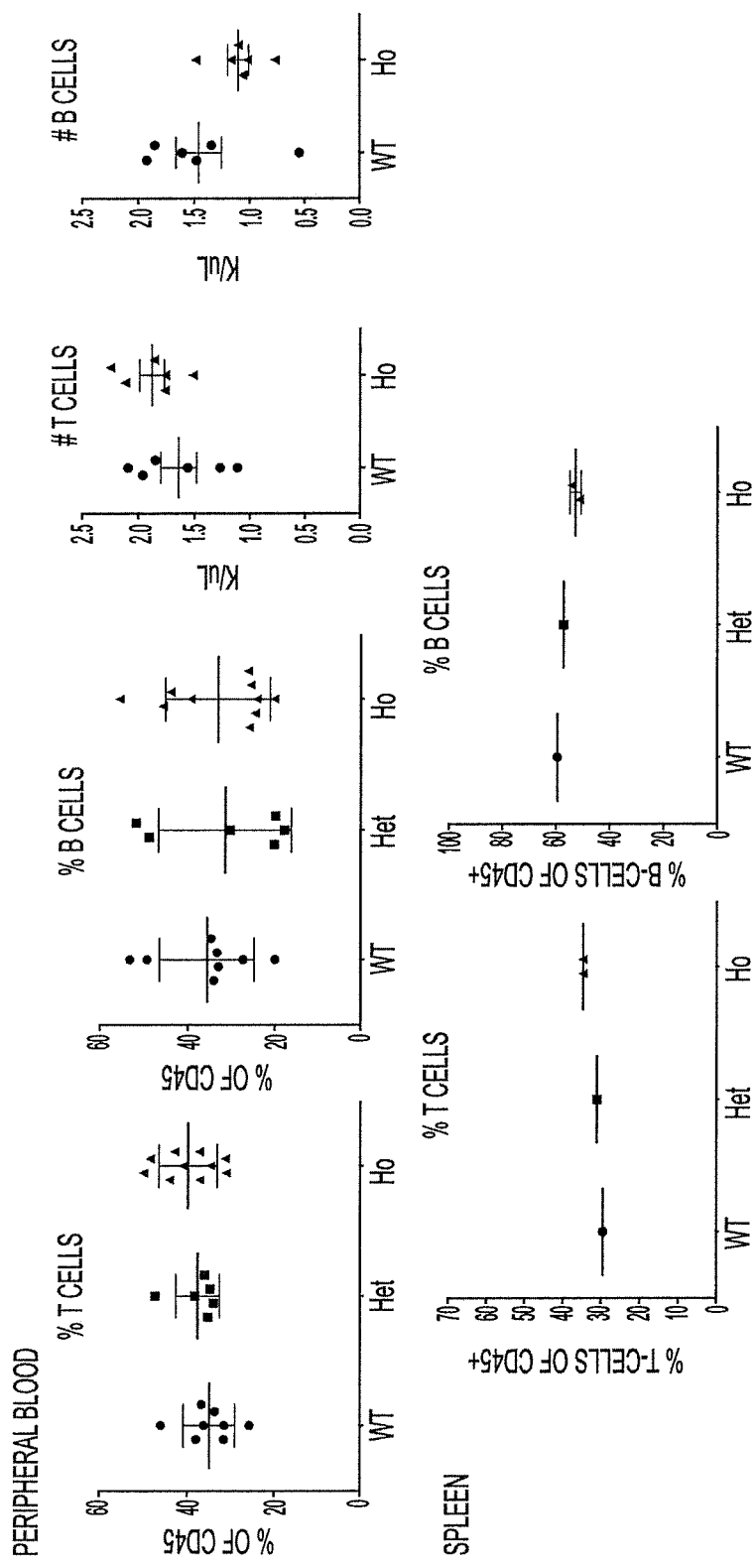
FIG. 5B, top row, is data depicting percentages as well as numbers of B and T cells in peripheral blood of indicated animals.

As demonstrated in FIGS. 5A and 5B, humanized CD3γδε mice appeared to have normal thymocyte development and normal T cell and B cell ratios in thymus, peripheral blood, and spleen. Additionally, T and B cell percentages appeared normal in lymph nodes, and absolute cell counts for spleen and lymph nodes (data not shown) were within normal range. CD4 and CD8 cell numbers in the blood were similar between the WT, Het, and Ho mice. Circulating white blood cells, lymphocytes, monocytes, neutrophils, eosinophils, and basophils all appeared within normal range (data not shown). Thus, normal immune cell development is observed in the humanized CD3εδγ mice.

In order to determine whether the humanized CD3εδγ mice exhibited a polyclonal Vβ CD4+ and CD8+ T cell repertoire, splenocytes were isolated from four humanized and five strain-matched control mice and examined for TCR Vβ usage. Spleens were harvested and single cell splenocytes prepared as described above. Cells were incubated for 10 minutes at room temperature with purified antibodies to CD16/CD32 (FcBlock; Biolegend) to block non-specific binding via Fc receptors, and then resuspended in a cocktail of directly conjugated antibodies to mouse CD4 (Biolegend) and mouse CD8 (Biolegend). The directly-conjugated antibodies to the TCR V13 were then added to the individual wells and incubated for 30 minutes at 4° C. Cells were washed with cold PBS and incubated with a viability dye (LIVE/DEAD Fixable Aqua Dead cell stain, Life Technologies) for 15 minutes at room temperature. Cells were washed with cold PBS containing 2% FBS then resuspended in buffer and fixed with BD Stabilization buffer before being analyzed by flow cytometry on a LSR Fortessa™ flow cytometer (BD Biosciences). CD4 and CD8 T cells were identified first by forward and side scatter gating, and then by gating on the live population. CD4 T cells (CD4+CD8−) and CD8 T cells (CD4−CD8+) were then examined for TCR Vβ usage.

Figure 5C:
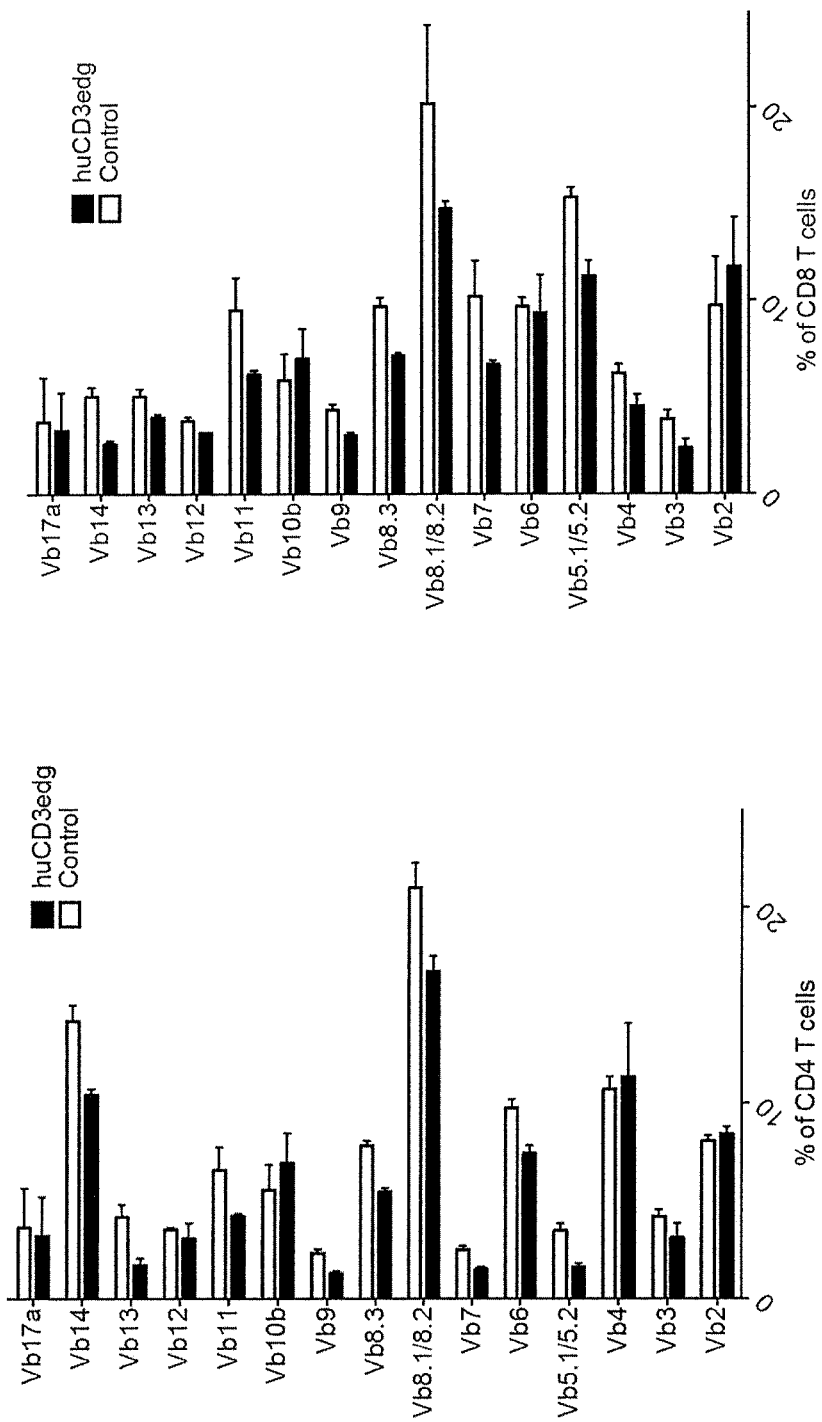
FIG. 5C shows Vβ repertoire polyclonality in CD4+ and CD8+ T cells obtained from the spleens of the humanized CD3γδε mice.

As can be seen from FIG. 5C, Vβ repertoire used by both CD4 and CD8 T cells in the humanized CD3εδγ mice shows polyclonality, with usage not significantly different from the strain-matched control mice.

Example 2.2

T Cell Response to Infection in Humanized CD3 Mice

To determine whether the humanized CD3 mice (humanized CD3εδγ mice) exhibited normal response to infection, the ability of humanized mice to clear lymphocytic choriomeningitis virus (LCMV) was tested. LCMV is a mouse tropic virus, where the fate of infection depends on the viral strain. Infection with Armstrong strain results in an acute infection, where mice can quickly mount a T cell response against the virus and clear the infection in about a week. On the other hand, Clone 13 virus cannot be cleared, and T cells become "exhausted" and chronic infection is established. As both chronic and acute infections depend on T cell activity, LCMV is an ideal model to test for T cell function.

6-8 week old humanized CD3 or strain matched control mice were infected with $2\times10^5$ ffu of Armstrong i.p. and/or $2\times10^6$ ffu of Clone 13 i.v. for Clone 13 infection, two weeks after infection spleens were harvested and virus titers were measured by plaque assay. Viral titers were similar in both control and huCD3 mice (FIG. 6A), indicating that CD3 humanization did not have an effect on the T-cell exhaustion phenotype, as T-cells can control the virus to similar levels in both strains of mice. For the Armstrong strain infection, two weeks after initial Amstrong strain infection, mice were challenged with Clone 13 and two weeks after Clone 13 challenge viral titers were measured in spleens. No virus was detected in either control or humanized CD3 mice (FIG. 6B). The data suggests that the acute Armstrong infection was cleared. In addition, this demonstrates that T-cell memory that was elicited from the Armstrong infection was sufficient to protect mice from the subsequent Clone 13 infection in both strains of mice.

Example 3

Humanized CD3 Mice as a Model for Testing Anti-CD3-Based Therapeutic Candidates

Example 3.1

Humanized CD3 Mouse for Testing Cynomolgus Monkey Cross-Reactive Anti-Human CD3 Antibodies The ability of different human restricted or cynomolgus cross-reactive anti-CD3 antibodies to bind splenocytes from wild type (WT) or humanized CD3γδε (Ho=homozygous, Het=heterozygous) mice was tested using fluorescence-activated cell sorting (FACS) analysis.

Freshly isolated splenocytes ($2 \times 10^5$ per well) were incubated with anti-CD3 antibodies (15 ug/ml) for 30 minutes at 4° C. Post incubation, cells were washed twice and appropriate secondary antibodies (e.g. fluorescent-tagged PE anti-human IgG and directly conjugated antibodies to T cell markers) were added and incubated for an additional 30 minutes at 4° C., then washed twice. The following antibodies were used: ah/mfCD3-2 and ah/mfCD3-1 are two antibodies that recognize both human and monkey CD3; ahCD3-2 and ahCD3-1 are two antibodies that only recognize human CD3, amCD3-2C11 is an antibody that recognizes mouse CD3 only, control human IgG is an unrelated control antibody, and $2^{nd}$ only is a secondary antibody only control. Cells were washed twice with cold PBS containing 1% BSA, resuspended in buffer and analyzed by flow cytometry on a FACSCanto II™ flow cytometer (BD Biosciences). T cells were identified as CD45+/TCRb+/B220–. Anti-mCD3-2C11 engineered to contain hIgG1 was used to identify T cells on WT mouse splenocytes.

Figure 7:
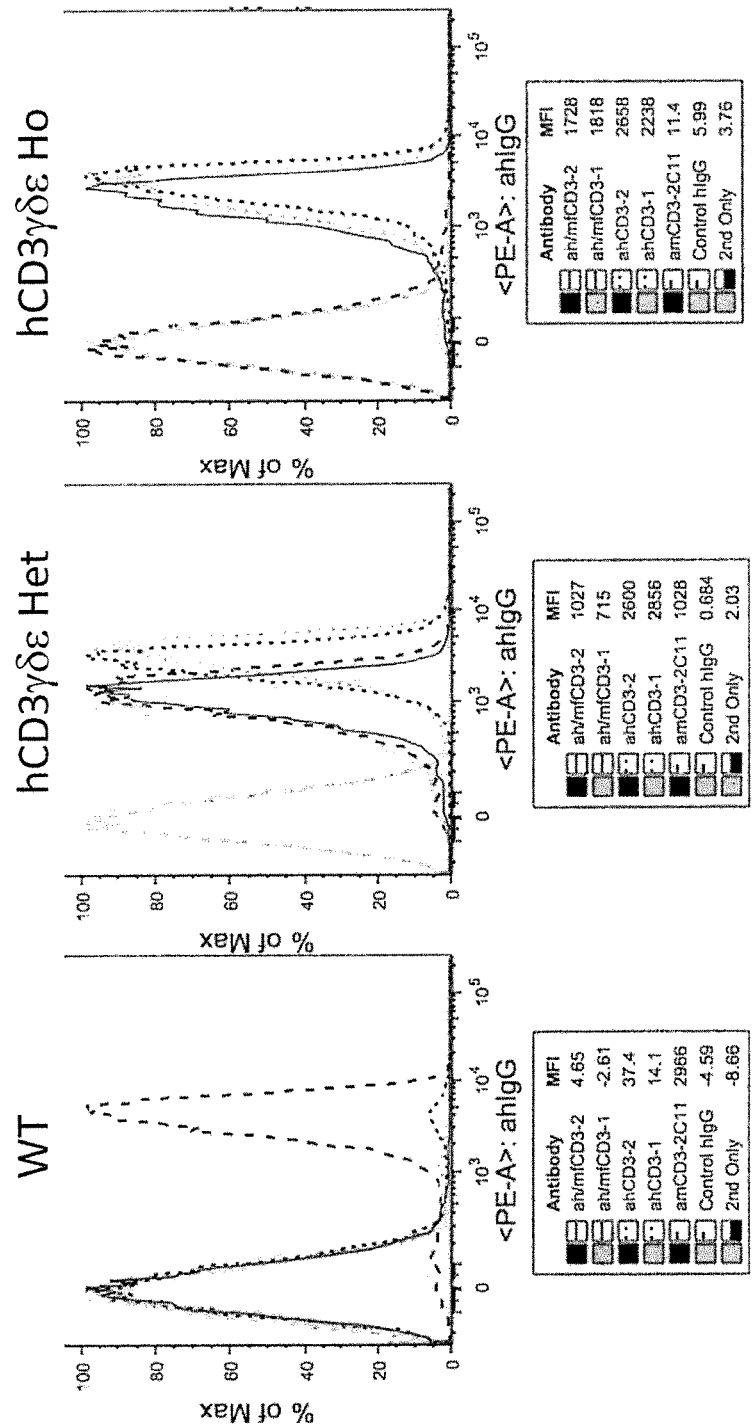
FIG. 7 is data from the FACS analysis of splenocytes from wild type (WT), heterozygous humanized CD3γδε (hCD3γδε Het), or homozygous humanized CD3γδε (hCD3γδεHo) mice sorted with two anti-human CD3 antibodies that also cross-react with monkey CD3 (ah/mfCD3-2 and ah/mfCD3-1), two anti-human CD3 antibodies that are human CD3 specific (ahCD3-1 and ahCD3-2), control anti-mouse CD3 (amCD3-2C11), unrelated control human IgG (control hIgG) and secondary only antibody control (2$^{nd}$ only). MFI values are listed in the tables below each graph.

As demonstrated in FIG. 7, anti-CD3 antibodies that recognized only human CD3 were able to bind CD3 on the surface of splenocytes from humanized CD3γδε mice; similarly anti-CD3 antibodies that recognized human and monkey CD3 were able to bind CD3 on the surface of humanized CD3γδε mice. Thus, mice humanized for all three CD3ε, CD3δ, and CD3γ are relevant for early pre-clinical studies of CD3-hased drug candidates which can be followed up by efficacy and toxicity studies in cynomolgus monkeys.

Example 3.2

T Cell Activation in Humanized CD3 Mice

The ability of anti-human CD3 antibodies to elicit immune response in humanized CD3 mice was tested. Mice humanized for CD3γδε (n of 2/group), were injected intraperitoneally with 10 ug of different human restricted or cynomolgus cross-reactive anti-CD3 antibodies (all hIgG1). To obtain cellular composition and plasma cytokine levels, blood was drawn into EDTA coated Microtainer tubes (BD) from the retro-orbital sinus starting 2 hours post injection. The number of peripheral T and B cells was assessed by FACS. Briefly, 50 ul whole blood was incubated for 30 minutes at 4° C. with a cocktail of directly conjugated antibodies to T and B cell markers. Red blood cells were removed by lysis with AKC Lysis buffer, and the labeled cells were washed one time with cold PBS containing 1% BSA. After washing, the cells were re-suspended in cold buffer and analyzed by flow cytometry on a FACSCANTO II™ flow cytometer (BD Biosciences). T cells were identified as live CD45+/TCRb+/B220–, and B cells were identified as live CD45+/TCRb–/B220+. Absolute cell counts were determined by adding a known quantity of Count-Bright TM Absolute Counting Beads. Plasma cytokine levels were assessed using a Mouse ProInflammatory 7-Plex Ultra-Sensitive Kit (Meso-Scale Discovery) from blood obtained 2 hours post injection.

Figure 8A:
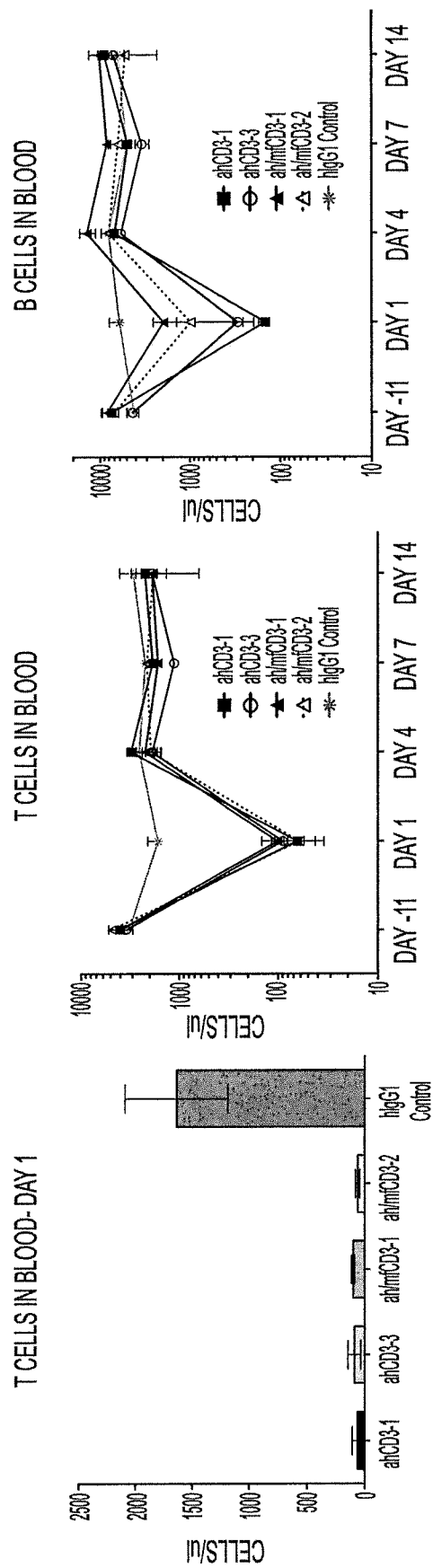
FIGS. 8A and B demonstrate responses to anti-CD3 antibodies in humanized CD3γδε mice.
Figure 8B:
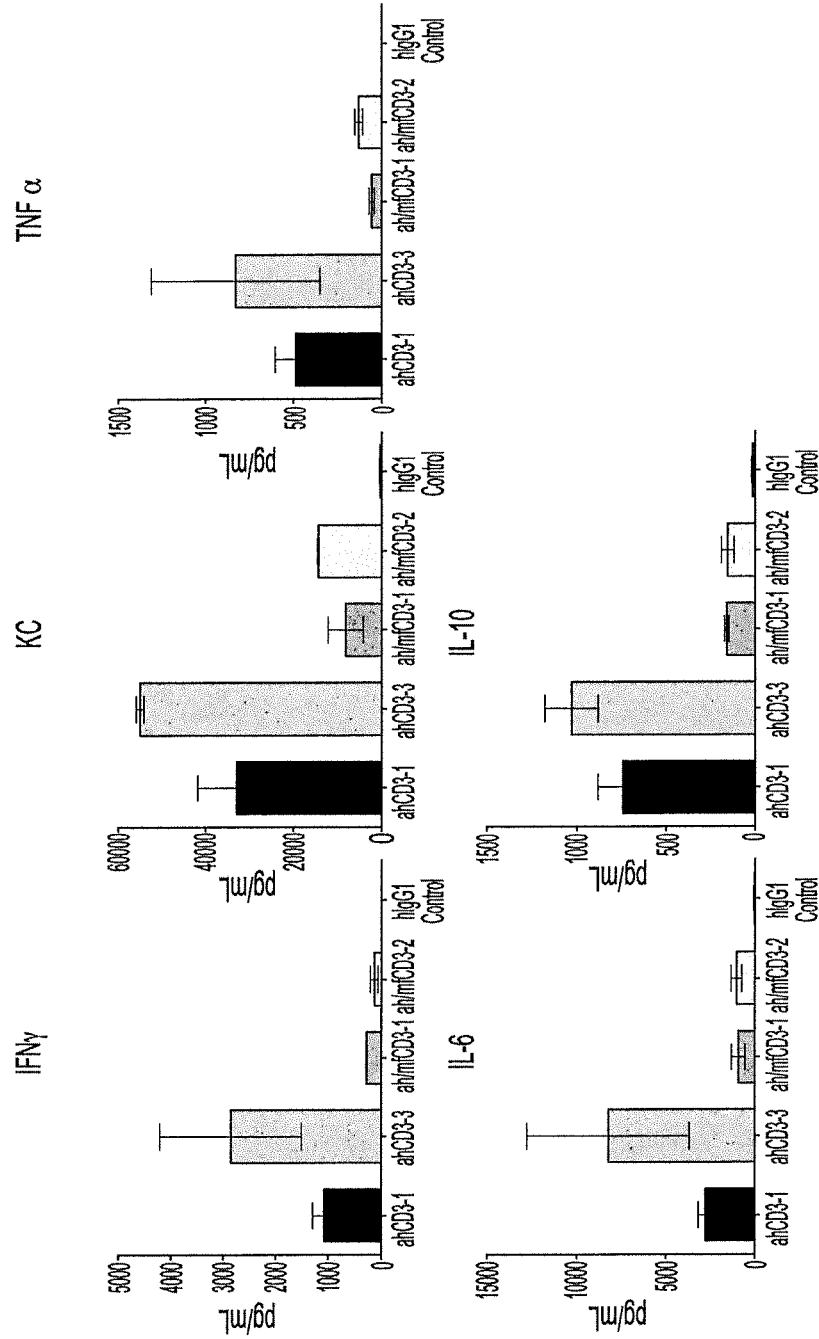
FIG. 8B depicts an increase in concentration of cytokines released (IFNγ, KC, TNFα, IL-6, and IL-10) 2 hours after treatment with indicated antibodies.

As demonstrated in FIG. 8A, injection of 10 ug of anti-CD3 antibodies induced a transient T and B cell depletion, which was largely restored by day 4 after initial antibody treatment. Additionally, injection of anti-CD3 antibodies (both anti-CD3 antibodies recognizing only human CD3 (ahCD3-1 and ahCD3-3) and anti-CD3 antibodies recognizing both human and monkey CD3 (ah/mfCD3-1 and ah/mfCD3-2)) induced cytokine production in CD3γδε humanized mice (FIG. 8B).

In addition, the ability of anti-human CD3, anti-human/cynomolgus CD3, or anti-mouse antibodies to induce proliferation of splenocytes obtained from wild type or humanized CD3γδε mice was assessed using ATP catalyzed quantification (CellTiter Glo®). The activation of mouse splenocytes results in the release of cytokines, which drive cellular proliferation. Proliferation data was acquired using the following protocol: splenocytes ($5 \times 10^5$/well) derived from wild type (WT) or humanized homozygous CD3γδε (hCD3γδεHo) were added to 96 well plates which had been coated overnight at 4° C. with decreasing amounts of human restricted, cynomolgus cross-reactive, or murine specific anti-CD3 antibodies. 500 ng/ml anti-mouse CD28 was added to the cultures, and the plates were incubated for 72 h at 37° C. Following incubation, CellTiter Glo® was added and luminescence was measured using a VICTOR X5 multi-label plate reader (PerkinElmer). The ECSO of cell viability (ATP catalyzed quantification) was determined using Prism (GraphPad Software, San Diego, CA). Values were calculated using a 4-parameter non-linear regression analysis.

Figure 9:
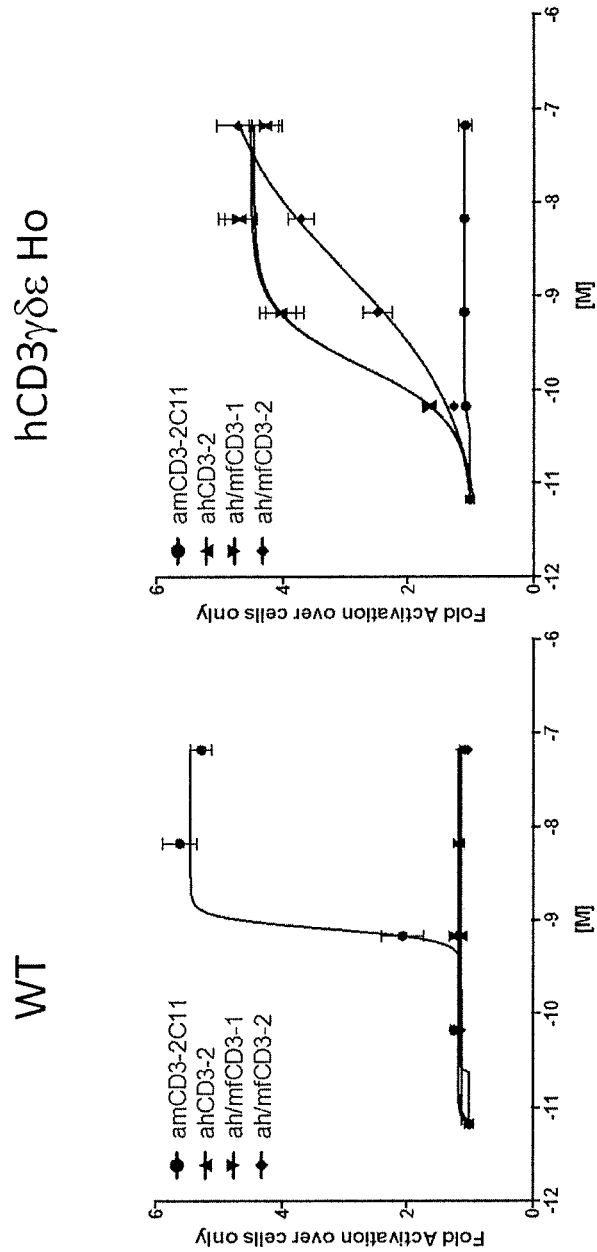
FIG. 9 demonstrates splenocytes proliferation (measured as fold activation over cells only) upon treatment with increasing amounts of indicated antibodies in wild type (WT) and humanized CD3γδε homozygous (hCD3γδε Ho) mice.

As demonstrated in FIG. 9, splenocytes from humanized CD3γδε mice were induced to proliferate by cynomolgus monkey-crossing CD3 antibodies.

A summary of various properties of WT and CD3γδε mice are presented in FIG. 10. As can be seen, lymphocytes from CD3γδε mice are able to bind anti-human CD3 antibodies and respond to anti-human CD3 antibodies, particularly those that are known to cross-react with monkey CD3, which is an important aspect for therapeutic agents as preclinical studies on drug candidates are often conducted in large animals such as cynomolgus monkeys.

Example 3.3

Tumor Depletion Studies in Humanized CD3 Mouse

Mice doubly humanized for both CD3 (humanized CD3γδε mice described above) and CD20 were produced by crossing mice humanized at CD3 locus with mice humanized at CD20 locus. The resultant animals expressed both humanized proteins. Specifically, to produce humanized CD20 mice, the entire mouse Ms4a1 (Cd20) coding region from the 2nd amino acid (first being Met which is in common) to 167 bp downstream 3' untranslated region, spanning 9312 bp (Murine Chr. 19) was replaced with the corresponding CD20 human coding region from the 2nd amino acid to 107 bp downstream 3'untranslated region, spanning 8482 bp (Human Chr. 11). Both mouse and human CD20 have six exons. The animals used in the experiment described below were homozygous for the replacements at both CD3 and CD20 loci and produced by crossing mice modified at the individual loci.

Figure 11A:
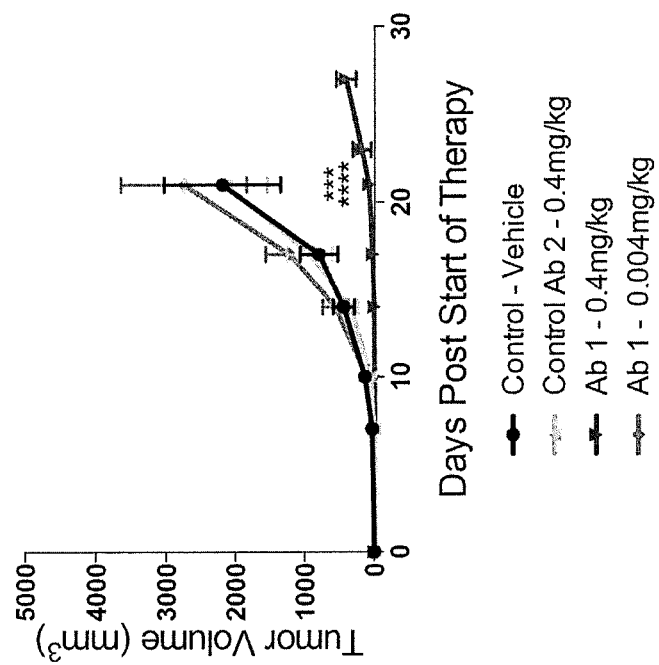
FIG. 11A demonstrates the effect of anti-CD3 antibody (Ab-1; bispecific antibody recognizing CD3 and CD20, tested at two different concentrations) on tumor volume of B16F10.9/CD20 tumors when treatment is initiated at the same time as tumor implantation (prophylactic model).

Humanized CD3/CD20 mice were implanted subcutaneously with 2×10⁵ B16F10.9 melanoma tumor cells transduced with human CD20. Starting at Day 0 (day of tumor transplantation), mice were treated intraperitoneally 2 times per week with either vehicle (PBS; n=5), 0.4 mg/kg control Ab 2 (control antibody that does not display cross-reactivity to CD20 antigen; n=5), 0.4 mg/kg of Ab 1 (anti-CD3/CD20 bispecific antibody, see WO2014121087A1, published Aug. 7, 2014, N=5), or 0.004 mg/kg Ab 1 (n=5). Tumor volumes were measured as indicated in FIG. 11A. Mice were sacrificed when tumors reached volume of greater than about 1500 mm³. As demonstrated in FIG. 11A, treatment with Ab 1 delayed tumor growth when treatment was initiated simultaneously with tumor transplantation.

Figure 11B:
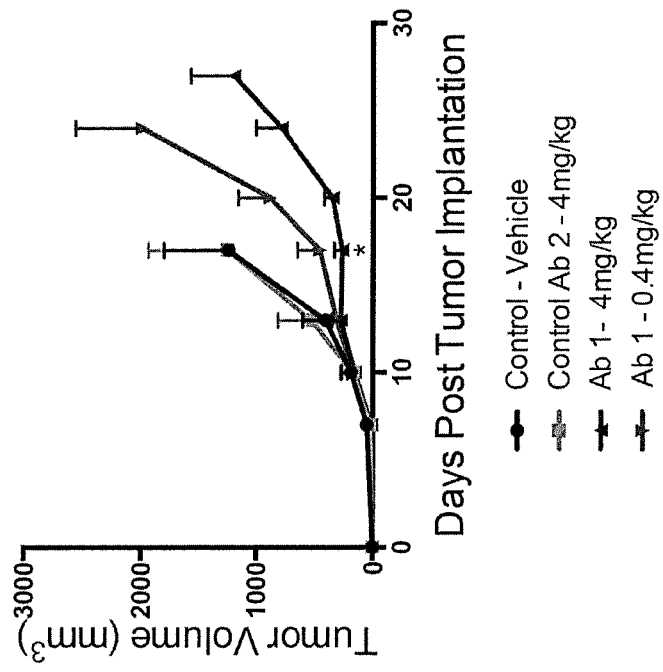
FIG. 11B demonstrates the effect of anti-CD3 antibody (Ab-1; bispecific antibody recognizing CD3 and CD20, tested at two different concentrations) on tumor volume of already established B16F10.9/CD20 tumors (therapeutic model).

In a separate experiment, ability of Ab 1 to inhibit tumor growth in an already established tumor was also tested (FIG. 11B). Humanized CD3/CD20 mice were implanted subcutaneously with 2×10⁵ B16F10.9 melanoma tumor cells expressing human CD20. On day 10 post tumor implantation, mice were randomized based on tumor size and organized into the following treatment groups, 5 mice in each group: vehicle (PBS), 4 mg/kg control Ab 2 (control antibody that does not display cross-reactivity to CD20 antigen), 4 mg/kg of Ab 1, or 0.4 mg/kg Ab 1. All mice were treated i.p. 2 times a week. Mice were sacrificed when tumors reached volume of greater than about 1500 mm³. As demonstrated in FIG. 11B, treatment with Ab 1 delayed tumor growth of already established tumors, demonstrating that the humanized CD3 mice are advantageous for early drug candidate studies.

Equivalents

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, accession numbers, websites and the like, patent applications and patents cited throughout this application are incorporated by reference herein in their entireties for all purposes to the same extent as if so individually denoted. If an accession number or other citation is associated with different content at different times, the content in effect at the effective filing date of the application is meant, the effective filing date being the filing date of the earliest priority application referencing the citation, or if none, the actual filing date.

Unless otherwise apparent from the context any embodiment, aspect, element, feature, step or the like can be combined with any other.

What is claimed is:

1. A targeting vector comprising:
   (i) a nucleic acid sequence encoding a functional chimeric human/mouse CD3ε protein that comprises an extracellular domain of a human CD3ε protein,
   (ii) a nucleic acid sequence encoding a functional chimeric human/mouse CD3δ protein that comprises an extracellular domain of a human CD3δ protein,
   (iii) a nucleic acid sequence encoding a functional chimeric human/mouse CD3γ protein that comprises an extracellular domain of a human CD3γ protein, and
   (iv) 5' and 3' homology arms that are homologous to a genomic region that is 5' to a mouse CD3ε gene and homologous to a genomic region that is 3' to a mouse CD3γ gene, respectively.

2. The targeting vector of claim 1, further comprising a selection cassette.

3. The targeting vector of claim 2, wherein the selection cassette is flanked by recombination sites that allow deletion of the selection cassette upon treatment with an appropriate recombinase.

4. The targeting vector of claim 1, wherein the selection cassette is upstream of (i) the nucleic acid sequence encoding the functional chimeric human/mouse CD3ε protein that comprises the extracellular domain of a human CD3ε protein.

5. The targeting vector of claim 1, wherein the functional chimeric human/mouse CD3ε protein comprises the sequence of SEQ ID NO:33, the functional chimeric human/mouse CD3δ protein comprises the sequence of SEQ ID NO:34, and/or the functional chimeric human/mouse CD3γ protein comprises the sequence of SEQ ID NO:35.

6. The targeting vector of claim 5, wherein the functional chimeric human/mouse CD3ε protein comprises the sequence of SEQ ID NO:33, the functional chimeric human/mouse CD3δ protein comprises the sequence of SEQ ID NO:34, and the functional chimeric human/mouse CD3γ protein comprises the sequence of SEQ ID NO:35.

7. The targeting vector of claim 1, wherein the functional chimeric human/mouse CD3ε protein comprises the sequence of SEQ ID NO:24, the functional chimeric human/mouse CD3δ protein comprises the sequence of SEQ ID NO:25, and/or the functional chimeric human/mouse CD3γ protein comprises the sequence of SEQ ID NO:26.

8. The targeting vector of claim 7, wherein the functional chimeric human/mouse CD3ε protein comprises the sequence of SEQ ID NO:24, the functional chimeric human/mouse CD3δ protein comprises the sequence of SEQ ID NO:25, and the functional chimeric human/mouse CD3γ protein comprises the sequence of SEQ ID NO:26.

9. An isolated mouse cell comprising the targeting vector of claim 1.

10. The isolated mouse cell of claim 9, wherein the cell is a mouse embryonic stem cell.

11. The isolated mouse cell of claim 9, wherein the cell is a mouse T cell.

12. The isolated mouse cell of claim 9, wherein the cell comprises a replacement of:
   (i) a genomic nucleic acid sequence encoding an endogenous mouse CD3γ protein with the nucleic acid sequence encoding the functional chimeric human/mouse CD3γ protein,
   (ii) a genomic nucleic acid sequence encoding an endogenous mouse CD3δ protein with the nucleic acid sequence encoding the functional chimeric human/mouse CD3δ protein, and
   (iii) a genomic nucleic acid sequence encoding an endogenous mouse CD3γ protein with the nucleic acid sequence encoding the functional chimeric human/mouse CD3γ protein.

13. The isolated mouse cell of claim 12, wherein the mouse cell is a T cell, and wherein the T cell comprises, on its surface, a functional chimeric human/mouse CD3 complex that (a) comprises the functional chimeric human/mouse CD3ε protein, the functional chimeric human/mouse CD3δ protein, and the functional chimeric human/mouse CD3γ protein and (b) is complexed with an endogenous mouse T-cell receptor.

14. The isolated mouse cell of claim 12, wherein the cell is heterozygous for the nucleic acid sequences encoding the functional chimeric human/mouse CD3 proteins.

15. The isolated mouse cell of claim 12, wherein the cell is homozygous for the nucleic acid sequences encoding the functional chimeric human/mouse CD3 proteins.

16. A method of modifying an isolated mouse ES cell, comprising introducing, into the isolated mouse ES cell, the targeting vector of claim 1.

17. The method of claim 16, wherein the introducing comprises electroporating the mouse ES cell in the presence of the targeting vector.

18. A method of making a genetically modified mouse, comprising:
   (a) introducing, into the genome of a mouse ES cell the targeting vector of claim 1; and
   (b) generating the genetically modified mouse from the mouse ES cell.

19. A method of making a genetically modified mouse, comprising generating the genetically modified mouse from the mouse ES cell of claim 10.

* * * * *

UNITED STATES PATENT AND TRADEMARK OFFICE
CERTIFICATE OF CORRECTION

PATENT NO. : 11,937,587 B2
APPLICATION NO. : 17/118241
DATED : March 26, 2024
INVENTOR(S) : Kara L. Olson et al.

It is certified that error appears in the above-identified patent and that said Letters Patent is hereby corrected as shown below:

In the Claims

Claim 12, Column 59, Line 27:
mouse CD3γ protein
Should be:
--mouse CD3ε protein--

Claim 12, Column 59, Line 29:
mouse CD3γ protein
Should be:
--mouse CD3ε protein--

Signed and Sealed this
Eleventh Day of June, 2024

Katherine Kelly Vidal
*Director of the United States Patent and Trademark Office*

SEQUENCE LISTING

```
<160> NUMBER OF SEQ ID NOS: 35

<210> SEQ ID NO 1
<211> LENGTH: 223
<212> TYPE: DNA
<213> ORGANISM: Artificial
<220> FEATURE:
<223> OTHER INFORMATION: synthetic

<400> SEQUENCE: 1
cgactttctt gacttctatt tgttaaacac tgtgcattca catcgaatgc tagaagtttc      60
ctcgtcccgc ttcctcctga attgcctggg atcctctgct tgatgccctg taggaaacgt     120
cctttcctgt ggtatagaaa tgactgctcg agataacttc gtataatgta tgctatacga     180
agttatatgc atggcctccg cgccgggttt tggcgcctcc cgc                       223

<210> SEQ ID NO 2
<211> LENGTH: 224
<212> TYPE: DNA
<213> ORGANISM: Artificial
<220> FEATURE:
<223> OTHER INFORMATION: synthetic

<400> SEQUENCE: 2
tgtatcttat catgtctgga ataacttcgt ataatgtatg ctatacgaag ttatgctagt      60
aactataacg gtcctaaggt agcgagctag ccttccacag acaccaatgt tcaaaatgga     120
ggcttggggg caaaattctt ttgctatgtc tctagtcgtc caaaaaatgg tcctaacttt     180
ttctgactcc tgcttgtcaa aaattgtggg ctcatagtta atgc                      224

<210> SEQ ID NO 3
<211> LENGTH: 227
<212> TYPE: DNA
<213> ORGANISM: Artificial
<220> FEATURE:
<223> OTHER INFORMATION: Synthetic
```

<400> SEQUENCE: 3

```
agggagagaat ggccttcatg cactccctcc tcacctccag cgccttgtgt tttccttgct    60
tagtgatttc ccctctcccc accccacccc ccacagtgtg tgagaactgc atggagatgg   120
atgtgatgtc ggtggccata atcatcattg ttgacatctg tatcactctg ggcttgctga   180
tggtcattta ttactggagc aagaatagga aggccaaggc caagcct               227
```

<210> SEQ ID NO 4
<211> LENGTH: 220
<212> TYPE: DNA
<213> ORGANISM: Artificial
<220> FEATURE:
<223> OTHER INFORMATION: Synthetic

<400> SEQUENCE: 4

```
gaaagagaga gtctttctgc taactaaccc ccagaaggcc ttccggtctc atgtcctgca    60
aagcagtaga cgcccaaagc caggagcaga gttgcgatga ggtcaatgaa gatgacacca   120
gccacggtgg ctggatccag ctccacacag ctctggcaca ctgtggggga agggaggaga   180
gaggagaggt tgagagcctt taagatcagg gaaccatcct                         220
```

<210> SEQ ID NO 5
<211> LENGTH: 226
<212> TYPE: DNA
<213> ORGANISM: Artificial
<220> FEATURE:
<223> OTHER INFORMATION: synthetic

<400> SEQUENCE: 5

```
caagagagac agaagtcaca agaaaaagcc ttcagaaagt tccccaccaa ctgcaggggt    60 caaggggac atgaggatgc cattcaagcg tcgacgagcg taggcagctt attgctctgc   120
atacttacag accatttgtg tagtaaggga catgatgccg agtgaaaggg gcaggagcaa   180
ccagagggag atttcaggaa gttctccagg gactcgaggt tcgtga                 226
```

<210> SEQ ID NO 6
<211> LENGTH: 224
<212> TYPE: DNA
<213> ORGANISM: Artificial
<220> FEATURE:
<223> OTHER INFORMATION: synthetic

<400> SEQUENCE: 6

```
gaagccccac ccagaaaggt aggacaaaga tcatagtcat atttacttca tccaggagag    60
aaacacagac acagccattg ccttggccat catctctctc catcttgacc tcacgtgatc   120
atggcgatcg cgagtgattt agtctacaat ccggaaaact aagtatagat actaccattt   180
tcatggattt ggatctttct tcatcttggc ctcaaataac catg                   224
```

<210> SEQ ID NO 7
<211> LENGTH: 216
<212> TYPE: DNA
<213> ORGANISM: Artificial
<220> FEATURE:
<223> OTHER INFORMATION: synthetic

<400> SEQUENCE: 7

```
gcattattgc agacaggcag gagaaaacga accaggaaaa acaactttcg caacctgaag    60
gtttgtctct ccttttccct acagtgtgtc agaactgcat tgaactaaat gcagccacca   120
```
tatctggctt tatcttcgct gaggtcatca gcatcttctt ccttgctctt ggtgtatatc    180
tcattgcggg acaggatgga caatacctg tcttaa    216

<210> SEQ ID NO 8
<211> LENGTH: 356
<212> TYPE: DNA
<213> ORGANISM: Artificial
<220> FEATURE:
<223> OTHER INFORMATION: synthetic

<400> SEQUENCE: 8
cgactttctt gacttctatt tgttaaacac tgtgcattca catcgaatgc tagaagtttc    60
ctcgtcccgc ttcctcctga attgcctggg atcctctgct tgatgccctg taggaaacgt    120
cctttcctgt ggtatagaaa tgactgctcg agataacttc gtataatgta tgctatacga    180
agttatgcta gtaactataa cggtcctaag gtagcgagct agccttccac agacaccaat    240
gttcaaaatg gaggcttggg ggcaaaattc ttttgctatg tctctagtcg tccaaaaaat    300
ggtcctaact ttttctgact cctgcttgtc aaaaattgtg gctcatagt taatgc    356

<210> SEQ ID NO 9
<211> LENGTH: 24
<212> TYPE: DNA
<213> ORGANISM: Artificial
<220> FEATURE:
<223> OTHER INFORMATION: synthetic

<400> SEQUENCE: 9
cctctgccat gtaggtttgt gtac    24

<210> SEQ ID NO 10
<211> LENGTH: 27
<212> TYPE: DNA
<213> ORGANISM: Artificial
<220> FEATURE:
<223> OTHER INFORMATION: synthetic

<400> SEQUENCE: 10
tgccgtgatg tttgttcaat gaccaaa    27

<210> SEQ ID NO 11
<211> LENGTH: 25
<212> TYPE: DNA
<213> ORGANISM: Artificial
<220> FEATURE:
<223> OTHER INFORMATION: synthetic

<400> SEQUENCE: 11
gttctgagaa aggcgttctt aagtg    25

<210> SEQ ID NO 12
<211> LENGTH: 21
<212> TYPE: DNA
<213> ORGANISM: Artificial
<220> FEATURE:
<223> OTHER INFORMATION: synthetic

<400> SEQUENCE: 12
ccaggcgtac ttgctgttct g    21

<210> SEQ ID NO 13
<211> LENGTH: 21
<212> TYPE: DNA
<213> ORGANISM: Artificial

```
<220> FEATURE:
<223> OTHER INFORMATION: synthetic

<400> SEQUENCE: 13
tgggcttacc atccaggacg a                                              21

<210> SEQ ID NO 14
<211> LENGTH: 25
<212> TYPE: DNA
<213> ORGANISM: Artificial
<220> FEATURE:
<223> OTHER INFORMATION: synthetic

<400> SEQUENCE: 14
gctactcttc ccacaaactg cttag                                          25

<210> SEQ ID NO 15
<211> LENGTH: 25
<212> TYPE: DNA
<213> ORGANISM: Artificial
<220> FEATURE:
<223> OTHER INFORMATION: synthetic

<400> SEQUENCE: 15
ccagcagtaa gttccactgt tctag                                          25

<210> SEQ ID NO 16
<211> LENGTH: 24
<212> TYPE: DNA
<213> ORGANISM: Artificial
<220> FEATURE:
<223> OTHER INFORMATION: synthetic

<400> SEQUENCE: 16
tgtagaaatg gctgtgaccc agca                                           24

<210> SEQ ID NO 17
<211> LENGTH: 20
<212> TYPE: DNA
<213> ORGANISM: Artificial
<220> FEATURE:
<223> OTHER INFORMATION: synthetic

<400> SEQUENCE: 17
gggctgtgtt gcagtatgac                                                20

<210> SEQ ID NO 18
<211> LENGTH: 23
<212> TYPE: DNA
<213> ORGANISM: Artificial
<220> FEATURE:
<223> OTHER INFORMATION: synthetic

<400> SEQUENCE: 18
accgtgcaag ttcattatcg aag                                            23

<210> SEQ ID NO 19
<211> LENGTH: 24
<212> TYPE: DNA
<213> ORGANISM: Artificial
<220> FEATURE:
<223> OTHER INFORMATION: synthetic

<400> SEQUENCE: 19
acgtgcttcc tgaaccctt gggt                                            24
```

```
<210> SEQ ID NO 20
<211> LENGTH: 22
<212> TYPE: DNA
<213> ORGANISM: Artificial
<220> FEATURE:
<223> OTHER INFORMATION: synthetic

<400> SEQUENCE: 20
tctcacatcc agaagcccta tc                                              22

<210> SEQ ID NO 21
<211> LENGTH: 24
<212> TYPE: DNA
<213> ORGANISM: Artificial
<220> FEATURE:
<223> OTHER INFORMATION: synthetic

<400> SEQUENCE: 21
cgagggatgt atcagtgtaa agga                                            24

<210> SEQ ID NO 22
<211> LENGTH: 29
<212> TYPE: DNA
<213> ORGANISM: Artificial
<220> FEATURE:
<223> OTHER INFORMATION: synthetic

<400> SEQUENCE: 22
cacagaacaa gtcaaaacca ctccaagtg                                       29

<210> SEQ ID NO 23
<211> LENGTH: 23
<212> TYPE: DNA
<213> ORGANISM: Artificial
<220> FEATURE:
<223> OTHER INFORMATION: synthetic

<400> SEQUENCE: 23
gctcaccaga acagcaaata ctg                                             23

<210> SEQ ID NO 24
<211> LENGTH: 207
<212> TYPE: PRT
<213> ORGANISM: Artificial
<220> FEATURE:
<223> OTHER INFORMATION: chimeric protein

<400> SEQUENCE: 24
```

Met Arg Trp Asn Thr Phe Trp Gly Ile Leu Cys Leu Ser Leu Leu Ala
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

```
Tyr Leu Arg Ala Arg Val Cys Glu Asn Cys Met Glu Met Asp Val Met
            115                 120                 125

Ser Val Ala Ile Ile Ile Val Asp Ile Cys Ile Thr Leu Gly Leu
    130                 135                 140

Leu Met Val Ile Tyr Tyr Trp Ser Lys Asn Arg Lys Ala Lys Ala Lys
145                 150                 155                 160

Pro Val Thr Arg Gly Thr Gly Ala Gly Ser Arg Pro Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Ala Val
        195                 200                 205

<210> SEQ ID NO 25
<211> LENGTH: 173
<212> TYPE: PRT
<213> ORGANISM: Artificial
<220> FEATURE:
<223> OTHER INFORMATION: chimeric protein

<400> SEQUENCE: 25

Met Glu His Ser Gly Ile Leu Ala Ser Leu Ile Leu Ile Ala Val Leu
1               5                   10                  15

Pro Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Val Ile Phe Ile Asp Leu
            100                 105                 110

Ile Ala Thr Leu Leu Leu Ala Leu Gly Val Tyr Cys Phe Ala Gly His
        115                 120                 125

Glu Thr Gly Arg Pro Ser Gly Ala Ala Glu Val Gln Ala Leu Leu Lys
    130                 135                 140

Asn Glu Gln Leu Tyr Gln Pro Leu Arg Asp Arg Glu Asp Thr Gln Tyr
145                 150                 155                 160

Ser Arg Leu Gly Gly Asn Trp Pro Arg Asn Lys Lys Ser
                165                 170

<210> SEQ ID NO 26
<211> LENGTH: 182
<212> TYPE: PRT
<213> ORGANISM: Artificial
<220> FEATURE:
<223> OTHER INFORMATION: chimeric protein

<400> SEQUENCE: 26

Met Glu Gln Arg Lys Gly Leu Ala Gly Leu Phe Leu Val Ile Ser Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45
```

```
Glu Ala Lys Asn Ile Thr Trp Phe Lys Asp Gly Lys Met Ile Gly Phe
         50                  55                  60

Leu Thr Glu Asp Lys Lys Trp Asn Leu Gly Ser Asn Ala Lys Asp
 65                  70                  75                  80

Pro Arg Gly Met Tyr Gln Cys Lys Gly Ser Gln Asn Lys Ser Lys Pro
                     85                  90                  95

Leu Gln Val Tyr Tyr Arg Met Cys Gln Asn Cys Ile Glu Leu Asn Ala
                100                 105                 110

Ala Thr Ile Ser Gly Phe Ile Phe Ala Glu Val Ile Ser Ile Phe Phe
                115                 120                 125

Leu Ala Leu Gly Val Tyr Leu Ile Ala Gly Gln Asp Gly Val Arg Gln
        130                 135                 140

Ser Arg Ala Ser Asp Lys Gln Thr Leu Leu Gln Asn Glu Gln Leu Tyr
145                 150                 155                 160

Gln Pro Leu Lys Asp Arg Glu Tyr Asp Gln Tyr Ser His Leu Gln Gly
                165                 170                 175

Asn Gln Leu Arg Lys Lys
            180

<210> SEQ ID NO 27
<211> LENGTH: 189
<212> TYPE: PRT
<213> ORGANISM: Mus musculus

<400> SEQUENCE: 27

Met Arg Trp Asn Thr Phe Trp Gly Ile Leu Cys Leu Ser Leu Leu Ala
 1               5                  10                  15

Val Gly Thr Cys Gln Asp Asp Ala Glu Asn Ile Glu Tyr Lys Val Ser
                20                  25                  30

Ile Ser Gly Thr Ser Val Glu Leu Thr Cys Pro Leu Asp Ser Asp Glu
            35                  40                  45

Asn Leu Lys Trp Glu Lys Asn Gly Gln Glu Leu Pro Gln Lys His Asp
     50                  55                  60

Lys His Leu Val Leu Gln Asp Phe Ser Glu Val Glu Asp Ser Gly Tyr
 65                  70                  75                  80

Tyr Val Cys Tyr Thr Pro Ala Ser Asn Lys Asn Thr Tyr Leu Tyr Leu
                 85                  90                  95

Lys Ala Arg Val Cys Glu Tyr Cys Val Glu Val Asp Leu Thr Ala Val
                100                 105                 110

Ala Ile Ile Ile Ile Val Asp Ile Cys Ile Thr Leu Gly Leu Leu Met
            115                 120                 125

Val Ile Tyr Tyr Trp Ser Lys Asn Arg Lys Ala Lys Ala Lys Pro Val
130                 135                 140

Thr Arg Gly Thr Gly Ala Gly Ser Arg Pro Arg Gly Gln Asn Lys Glu
145                 150                 155                 160

Arg Pro Pro Pro Val Pro Asn Pro Asp Tyr Glu Pro Ile Arg Lys Gly
                165                 170                 175

Gln Arg Asp Leu Tyr Ser Gly Leu Asn Gln Arg Ala Val
            180                 185

<210> SEQ ID NO 28
<211> LENGTH: 207
<212> TYPE: PRT
<213> ORGANISM: homo sapiens

<400> SEQUENCE: 28
```

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
                35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
                195                 200                 205

<210> SEQ ID NO 29
<211> LENGTH: 173
<212> TYPE: PRT
<213> ORGANISM: mus musculus

<400> SEQUENCE: 29

Met Glu His Ser Gly Ile Leu Ala Ser Leu Ile Leu Ile Ala Val Leu
1               5                   10                  15

Pro Gln Gly Ser Pro Phe Lys Ile Gln Val Thr Glu Tyr Glu Asp Lys
                20                  25                  30

Val Phe Val Thr Cys Asn Thr Ser Val Met His Leu Asp Gly Thr Val
            35                  40                  45

Glu Gly Trp Phe Ala Lys Asn Lys Thr Leu Asn Leu Gly Lys Gly Val
    50                  55                  60

Leu Asp Pro Arg Gly Ile Tyr Leu Cys Asn Gly Thr Glu Gln Leu Ala
65                  70                  75                  80

Lys Val Val Ser Ser Val Gln Val His Tyr Arg Met Cys Gln Asn Cys
                85                  90                  95

Val Glu Leu Asp Ser Gly Thr Met Ala Gly Val Ile Phe Ile Asp Leu
            100                 105                 110

Ile Ala Thr Leu Leu Leu Ala Leu Gly Val Tyr Cys Phe Ala Gly His
        115                 120                 125

Glu Thr Gly Arg Pro Ser Gly Ala Ala Glu Val Gln Ala Leu Leu Lys
    130                 135                 140

Asn Glu Gln Leu Tyr Gln Pro Leu Arg Asp Arg Glu Asp Thr Gln Tyr
145                 150                 155                 160

Ser Arg Leu Gly Gly Asn Trp Pro Arg Asn Lys Lys Ser
                165                 170
```

<210> SEQ ID NO 30
<211> LENGTH: 171
<212> TYPE: PRT
<213> ORGANISM: homo sapiens

<400> SEQUENCE: 30

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
            35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 31
<211> LENGTH: 182
<212> TYPE: PRT
<213> ORGANISM: mus musculus

<400> SEQUENCE: 31

Met Glu Gln Arg Lys Gly Leu Ala Gly Leu Phe Leu Val Ile Ser Leu
1               5                   10                  15

Leu Gln Gly Thr Val Ala Gln Thr Asn Lys Ala Lys Asn Leu Val Gln
                20                  25                  30

Val Asp Gly Ser Arg Gly Asp Gly Ser Val Leu Leu Thr Cys Gly Leu
            35                  40                  45

Thr Asp Lys Thr Ile Lys Trp Leu Lys Asp Gly Ser Ile Ile Ser Pro
        50                  55                  60

Leu Asn Ala Thr Lys Asn Thr Trp Asn Leu Gly Asn Asn Ala Lys Asp
65                  70                  75                  80

Pro Arg Gly Thr Tyr Gln Cys Gln Gly Ala Lys Glu Thr Ser Asn Pro
                85                  90                  95

Leu Gln Val Tyr Tyr Arg Met Cys Glu Asn Cys Ile Glu Leu Asn Ile
            100                 105                 110

Gly Thr Ile Ser Gly Phe Ile Phe Ala Glu Val Ile Ser Ile Phe Phe
        115                 120                 125

Leu Ala Leu Gly Val Tyr Leu Ile Ala Gly Gln Asp Gly Val Arg Gln
130                 135                 140

Ser Arg Ala Ser Asp Lys Gln Thr Leu Leu Gln Asn Glu Gln Leu Tyr

```
                145                 150                 155                 160
Gln Pro Leu Lys Asp Arg Glu Tyr Asp Gln Tyr Ser His Leu Gln Gly
                    165                 170                 175
Asn Gln Leu Arg Lys Lys
            180

<210> SEQ ID NO 32
<211> LENGTH: 182
<212> TYPE: PRT
<213> ORGANISM: homo sapiens

<400> SEQUENCE: 32

Met Glu Gln Gly Lys Gly Leu Ala Val Leu Ile Leu Ala Ile Ile Leu
1               5                   10                  15
Leu Gln Gly Thr Leu Ala Gln Ser Ile Lys Gly Asn His Leu Val Lys
                20                  25                  30
Val Tyr Asp Tyr Gln Glu Asp Gly Ser Val Leu Leu Thr Cys Asp Ala
            35                  40                  45
Glu Ala Lys Asn Ile Thr Trp Phe Lys Asp Gly Lys Met Ile Gly Phe
        50                  55                  60
Leu Thr Glu Asp Lys Lys Lys Trp Asn Leu Gly Ser Asn Ala Lys Asp
65                  70                  75                  80
Pro Arg Gly Met Tyr Gln Cys Lys Gly Ser Gln Asn Lys Ser Lys Pro
                85                  90                  95
Leu Gln Val Tyr Tyr Arg Met Cys Gln Asn Cys Ile Glu Leu Asn Ala
            100                 105                 110
Ala Thr Ile Ser Gly Phe Leu Phe Ala Glu Ile Val Ser Ile Phe Val
        115                 120                 125
Leu Ala Val Gly Val Tyr Phe Ile Ala Gly Gln Asp Gly Val Arg Gln
    130                 135                 140
Ser Arg Ala Ser Asp Lys Gln Thr Leu Leu Pro Asn Asp Gln Leu Tyr
145                 150                 155                 160
Gln Pro Leu Lys Asp Arg Glu Asp Asp Gln Tyr Ser His Leu Gln Gly
                165                 170                 175
Asn Gln Leu Arg Arg Asn
            180

<210> SEQ ID NO 33
<211> LENGTH: 113
<212> TYPE: PRT
<213> ORGANISM: homo sapiens

<400> SEQUENCE: 33

Gly Val Trp Gly Gln Asp Gly Asn Glu Glu Met Gly Gly Ile Thr Gln
1               5                   10                  15
Thr Pro Tyr Lys Val Ser Ile Ser Gly Thr Thr Val Ile Leu Thr Cys
                20                  25                  30
Pro Gln Tyr Pro Gly Ser Glu Ile Leu Trp Gln His Asn Asp Lys Asn
            35                  40                  45
Ile Gly Gly Asp Glu Asp Asp Lys Asn Ile Gly Ser Asp Glu Asp His
        50                  55                  60
Leu Ser Leu Lys Glu Phe Ser Glu Leu Glu Gln Ser Gly Tyr Tyr Val
65                  70                  75                  80
Cys Tyr Pro Arg Gly Ser Lys Pro Glu Asp Ala Asn Phe Tyr Leu Tyr
                85                  90                  95
Leu Arg Ala Arg Val Cys Glu Asn Cys Met Glu Met Asp Val Met Ser
```

```
                100             105             110
Val

<210> SEQ ID NO 34
<211> LENGTH: 87
<212> TYPE: PRT
<213> ORGANISM: homo sapiens

<400> SEQUENCE: 34

Val Ser Pro Phe Lys Ile Pro Ile Glu Glu Leu Glu Asp Arg Val Phe
1               5                   10                  15

Val Asn Cys Asn Thr Ser Ile Thr Trp Val Glu Gly Thr Val Gly Thr
            20                  25                  30

Leu Leu Ser Asp Ile Thr Arg Leu Asp Leu Gly Lys Arg Ile Leu Asp
        35                  40                  45

Pro Arg Gly Ile Tyr Arg Cys Asn Gly Thr Asp Ile Tyr Lys Asp Lys
    50                  55                  60

Glu Ser Thr Val Gln Val His Tyr Arg Met Cys Gln Ser Cys Val Glu
65                  70                  75                  80

Leu Asp Pro Ala Thr Val Ala
                85

<210> SEQ ID NO 35
<211> LENGTH: 97
<212> TYPE: PRT
<213> ORGANISM: homo sapiens

<400> SEQUENCE: 35

Thr Leu Ala Gln Ser Ile Lys Gly Asn His Leu Val Lys Val Tyr Asp
1               5                   10                  15

Tyr Gln Glu Asp Gly Ser Val Leu Leu Thr Cys Asp Ala Glu Ala Lys
            20                  25                  30

Asn Ile Thr Trp Phe Lys Asp Gly Lys Met Ile Gly Phe Leu Thr Glu
        35                  40                  45

Asp Lys Lys Lys Trp Asn Leu Gly Ser Asn Ala Lys Asp Pro Arg Gly
    50                  55                  60

Met Tyr Gln Cys Lys Gly Ser Gln Asn Lys Ser Lys Pro Leu Gln Val
65                  70                  75                  80

Tyr Tyr Arg Met Cys Gln Asn Cys Ile Glu Leu Asn Ala Ala Thr Ile
                85                  90                  95

Ser
```